(12) United States Patent
Gruskin et al.

(10) Patent No.: US 8,968,735 B2
(45) Date of Patent: *Mar. 3, 2015

(54) COMPOSITIONS AND METHODS INCLUDING A RECOMBINANT HUMAN MAB THAT PROMOTES CNS REMYELINATION

(71) Applicants: Acorda Therapeutics, Inc., Ardsley, NY (US); Mayo Foundation for Medical Education and Research, Rochester, MN (US)

(72) Inventors: Elliot A. Gruskin, Malvern, PA (US); Eric Chojnicki, Houston, TX (US); Arthur E. Warrington, Rochester, MN (US); Allan J. Bieber, Rochester, MN (US); Moses Rodriguez, Rochester, MN (US)

(73) Assignees: Mayo Foundation for Medical Education & Research, Rochester, MN (US); Acorda Therapeutics, Inc., Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/788,529

(22) Filed: Mar. 7, 2013

(65) Prior Publication Data

US 2013/0309240 A1 Nov. 21, 2013

Related U.S. Application Data

(63) Continuation of application No. 10/557,115, filed as application No. PCT/US2004/015436 on May 17, 2004, now Pat. No. 8,460,665.

(60) Provisional application No. 60/471,235, filed on May 16, 2003.

(51) Int. Cl.
*A61K 39/395* (2006.01)
*A61K 31/573* (2006.01)
*C07K 16/18* (2006.01)
*A61K 39/00* (2006.01)

(52) U.S. Cl.
CPC ......... *A61K 39/39533* (2013.01); *A61K 31/573* (2013.01); *A61K 39/39541* (2013.01); *A61K 2039/505* (2013.01); *A61K 2039/545* (2013.01); *C07K 16/18* (2013.01); *C07K 2317/21* (2013.01); *C07K 2317/56* (2013.01)
USPC ................... 424/141.1; 424/135.1; 424/172.1

(58) Field of Classification Search
CPC .................................................... A61K 39/39
See application file for complete search history.

(56) References Cited

U.S. PATENT DOCUMENTS

| 4,472,500 A | 9/1984 | Milstein et al. |
| 4,493,795 A | 1/1985 | Nestor, Jr. et al. |
| 4,816,397 A | 3/1989 | Boss et al. |
| 5,190,752 A | 3/1993 | Möller et al. |
| 5,256,771 A | 10/1993 | Tsay et al. |
| 5,510,465 A | 4/1996 | Tsay et al. |
| 5,612,033 A | 3/1997 | Tsay et al. |

FOREIGN PATENT DOCUMENTS

WO    WO 01/85797    11/2001

OTHER PUBLICATIONS

Abo et al (1981) J. Immunol. 127:1024-1029s.
Asakura et al (1997) J. Neurochem 68:2281-2290.
Bansal et al (1989) J. Neurosci. Res. 24:548-557.
Ciric, B. et al. (2001) Blood 97:321-323.
Eisenbarth et al (1979) Proc. Natl. Acad. Sci. USA 76:4913-4917.
Fredman et al (1984) Arch. Biochem. Biophys. 233:661-666.
Gard et al. (1990) Neuron, 5:615-625.
Kasai et al (1983) Brain Res. 277:155-158.
Keilhauer et al (1985) Nature 316:728-730.
Kruse et al (1984) Nature 311:153-155.
Kruse et al (1985) Nature 316:146-148.
Kuo et al (1993) Blood 82:845.
Lebkowski et al. (1988) Mol. Cell. Biol. 8:3988-3996.
Mann et al (1983) Cell 33:153.
Markowitz et al (1988) J. Virol. 62:1120.
McGarry et al (1983) Nature 306:376-378.
McGarry et al (1985) J. Neuroimmunol 10:101-114.
Miller et al (1994) J. Neurosci. 14:6230-6238.
Schachner, J. (1982) Neurochem 39:1-8.
Simonsen, C. et al. (1983) PNAS USA 80:2495-2499.
Sommer et al. (1981) Dev. Biol. 83:311-327.
Tsujimoto, Y. et al. (1984) Nucleic Acids Res. 12:8407-8414.
Warrington, A. et al. (1992) J. Neurosci Res. 33:338-353.
Warrington et al. (2000) Proc Natl Acad Sci USA 97(12):6820-6825.

*Primary Examiner* — John Ulm
(74) *Attorney, Agent, or Firm* — Klauber & Jackson LLC

(57) ABSTRACT

Antibodies, and particularly human antibodies, are disclosed that demonstrate activity in the treatment of demyelinating diseases as well as other diseases of the central nervous system that are of viral, bacterial or idiopathic origin, including neural dysfunction caused by spinal cord injury. Neuromodulatory agents are set forth that include and comprise a material selected from the group consisting of an antibody capable of binding structures or cells in the central nervous system, a peptide analog, a hapten, active fragments thereof, agonists thereof, mimics thereof, monomers thereof and combinations thereof. Methods are described for treating demyelinating diseases, and diseases of the central nervous system of humans and domestic animals, using polyclonal IgM antibodies and human monoclonal antibodies sHIgm22(LYM 22), sHIgm46(LYM46) ebvHIgM MSI19D10, CB2bG8, AKJR4, CB2iE12, CB2iE7, MSI19E5 and MSI10E10, active fragments thereof and the like. The invention also extends to the use of human antibodies, fragments, peptide derivatives and like materials, and their use in above referenced therapeutic applications, and to pharmaceutical compositions containing them, that may be administered in desirably low doses to treat conditions involving demyelination and to promote remyelination.

13 Claims, 6 Drawing Sheets

```
/FR1------------------------------------------------
  1    2    3    4    5    6    7    8    9   10   11   12   13   14   15
  Q    V    Q    L    V    E    S    G    G    G    V    V    Q    P    G
 CAG  GTG  CAG  CTG  GTG  GAG  TCT  GGG  GGA  GGC  GTG  GTC  CAG  CCT  GGG
Clone A sH-IgM.22 VH                       G
Clone B sH-IgM.22 VH
----------------------------------------------------
 16   17   18   19   20   21   22   23   24   25   26   27   28   29   30
  R    S    L    R    L    S    C    A    A    S    G    F    T    F    S
 AGG  TCC  CTG  AGA  CTC  TCC  TGT  GCA  GCC  TCT  GGA  TTC  ACC  TTC  AGT /CDR1--------------/FR2-----------------------------
 31   32   33   34   35   36   37   38   39   40   41   42   43   44   45
  S    S    G    M    H    W    V    R    Q    A    P    G    K    G    L
 AGC  TAT  GGC  ATG  CAC  TGG  GTC  CGC  CAG  GCT  CCA  GGC  AAG  GGG  CTG
       C                                      A
       C
---------------/CDR2--------------------------------
 46   47   48   49   50   51   52  52A   53   54   55   56   57   58   59
  E    W    V    A   V(I)   I    S    Y    D    G    S    R    K    Y    Y
 GAG  TGG  GTG  GCA  GTT  ATA  TCA  TAT  GAT  GGA  AGT  AAT  AAA  TAC  TAT
                      T                                 GG
                    A C    T                            GG
---------------------/FR3---------------------------
 60   61   62   63   64   65   66   67   68   69   70   71   72   73   74
  A    D    S    V    K    G    R    F    T    I    S    R    D    N    S
 GCA  GAC  TCC  GTG  AAG  GGC  CGA  TTC  ACC  ATC  TCC  AGA  GAC  AAT  TCC
                                                                        C
                                                                        C 75   76   77   78   79   80   81   82  82A  82B  82C   83   84   85   86
  K    N    T    L    Y    L    Q    M    N    S    L    T    A   D(E)   D
 AAG  AAC  ACG  CTG  TAT  CTG  CAA  ATG  AAC  AGC  CTG  AGA  GCT  GAG  GAC
            T                                            CG         C
            T    C
-----------------------/CDR3------------------------
 87   88   89   90   91   92   93   94   95   96   97   98   99  100 100A
  T    A    V    Y    Y    C    A    K    G    V    T    G    S    P    T
 ACG  GCT  GTG  TAT  TAC  TGT  GCG  AAA  GAG  GTG  ACT  GCT  ATT  CCC  TAC
                      T                        GA             G    G    G  ACG
                                               GA             G    G    G  ACG
----------/FR4--------------------------------------
100B 101  102  103  104  105  106  107  108  109  110  111  112  113
  L    D    Y    W    G    Q    G    T    L    V    T    V    S    S
 TTT  GAC  TAC  TGG  GGC  CAG  GGA  ACC  CTG  GTC  ACC  GTC  TCC  TCA
 C                                                                 G
 C                                                                 G
```

Figure 5

```
/FR1---------------------------------------------------------
   1    2    3    4    5    6    7    8    9   11   12   13   14   15   16
   Q    S    V    L    T    Q    P    P    S    V    S    A    A    P    G
  CAG  TCT  GTG  TTG  ACG  CAG  CCG  CCC  TCA  GTG  TCT  GCG  GCC  CCA  GGA
Clone I sH-IgM.22 Vλ        G              T                   T
Clone II sH-IgM.22 Vλ       G              T                   T
--------------------------------/CDR1-------------------------
  17   18   19   20   21   22   23   24   25   26   27  27A  27B   28   29
   Q    K    V    T    I    S    C    S    G    S    S    S    N    I    G
  CAG  AAG  GTC  ACC  ATC  TCC  TGC  TCT  GGA  AGC  AGC  TCC  AAC  ATT  GGG
                                                                           C
                                                                           C
----------------------/FR2------------------------------------
  30   31   32   33   34   35   36   37   38   39   40   41   42   43   44
   N    N    F    V    S    W    Y    Q    Q    L    P    G    T    A    P
  AAT  AAT  TAT  GTA  TCC  TGG  TAC  CAG  CAG  CTC  CCA  GGA  ACA  GCC  CCC
             T                                       A
             T                                       A
----------------/CDR2---------------------------/FR3----------
  45   46   47   48   49   50   51   52   53   54   55   56   57   58   59
  R(K)  L    L    I    Y    D    I    T    K    R    P    S    G    I    P
  AAA  CTC  CTC  ATT  TAT  GAC  AAT  AAT  AAG  CGA  CCC  TCA  GGG  ATT  CCT
   G                             T    C
                                 T    C
--------------------------------------------------------------
  60   61   62   63   64   65   66   67   68   69   70   71   72   73   74
   D    R    F    S    G    S    K    S    G    T    S    A    T    L    G
  GAC  CGA  TTC  TCT  GGC  TCC  AAG  TCT  GGC  ACG  TCA  GCC  ACC  CTG  GGC ---------------------------------------------------/CDR3-----
  75   76   77   78   79   80   81   82   83   84   85   86   87   88   89
   I    T    G    L    Q    T    G    D    E    A    D    Y    Y    C   G(E)
  ATC  ACC  GGA  CTC  CAG  ACT  GGG  GAC  GAG  GCC  GAT  TAT  TAC  TGC  GGA
                                                                           A
---------------------------------/FR4-------------------------
  90   91   92   93   94   95  95A  95B   96   97   98   99  100  101  102
   T    W    D    S    S    L    S    A    V    V    F    G    G    G    T
  ACA  TGG  GAT  AGC  AGC  CTG  ...  ..T  GTG  GTA  TTC  GGC  GGA  GGG  ACC
                              AGT   GC                             G
                              AGT   GC                             G
---------------------/Cλ--------
 103  104  105  106 106A 107  108  109  110
   K    L    T    V    L    G    Q    P    K
  AAG  CTG  ACC  GTC  CTA  GGT  CAG  CCC  AAG
```

Figure 6

COMPOSITIONS AND METHODS INCLUDING A RECOMBINANT HUMAN MAB THAT PROMOTES CNS REMYELINATION

CROSS REFERENCE TO RELATED APPLICATIONS

The present application is a Continuation Application of U.S. application Ser. No. 10/557,115, filed on Dec. 13, 2006, now U.S. Pat. No. 8,460,665, which in turn, claims priority from Application Serial No. PCT/US2004/015436, filed on May 17, 2004, which claims priority from U.S. Provisional Application Ser. No. 60/471,235 filed May 16, 2003. Applicants claim the benefits of 35 U.S.C. §119 and §120 as to the said Applications, and the entire disclosures of the applications are incorporated herein by reference in their entireties.

FIELD OF THE INVENTION

The present invention relates generally to the field of neurobiology, and more particularly to the identification of recombinantly produced antibodies that play a role in central nervous system function and therapy. The invention also relates to therapeutic materials and methods, including by way of example, pharmaceutical compositions, methods of treatment of diseases associated with neurological impairment, methods of regeneration and restoration of neural function, screening assays and vaccines.

BACKGROUND OF THE INVENTION

Multiple sclerosis (MS) is a chronic, frequently progressive, inflammatory central nervous system (CNS) disease characterized pathologically by primary demyelination, usually without initial axonal injury. The etiology and pathogenesis of MS are unknown. Several immunological features of MS, and its moderate association with certain major histocompatibility complex alleles, has prompted the speculation that MS is an immune-mediated disease.

An autoimmune hypothesis is supported by the experimental autoimmune (allergic) encephalomyelitis (EAE) model, where injection of certain myelin components into genetically susceptible animals leads to T cell-mediated CNS demyelination. However, specific autoantigens and pathogenic myelin-reactive T cells have not been definitively identified in the CNS of MS patients, nor is MS associated with other autoimmune diseases. An alternative hypothesis, based upon epidemiological data, is that an environmental factor, perhaps an unidentified virus, precipitates an inflammatory response in the CNS, which leads to either direct or indirect ("bystander") myelin destruction, potentially with an induced autoimmune component. This hypothesis is supported by evidence that several naturally occurring viral infections, both in humans and animals, can cause demyelination. One commonly utilized experimental viral model is induced by Theiler's murine encephalomyelitis virus (TMEV) (Dal Canto, M. C., and Lipton, H. L., *Am. J. Path.*, 88:497-500 (1977)).

The limited efficacy of current therapies for MS and other demyelinating diseases, has stimulated interest in novel therapies to ameliorate these diseases. However, due to the apparently complex etiopathogenesis of these diseases, potentially involving both environmental and autoimmune factors, the need still exists for an effective treatment of these demyelinating disorders.

rHIgM22 is a recombinant human IgM antibody that binds to mature oligodendrocytes and myelin of both rodents and humans, and promotes the synthesis of new myelin in in vivo models of demyelination. The standard dose of remyelination-promoting mAbs in prior studies has been 25 mg/kg, administered I.P. This dose, if extrapolated to humans, would be impractical.

Accordingly, a need exists to develop a practical, safe and efficacious treatment regimen for CNS disorders, particularly those involving demyelination and/or remyelination, and it is toward the fulfillment of that need that the present invention is directed.

The citation of any reference herein should not be construed as an admission that such reference is available as "Prior Art" to the instant application.

SUMMARY OF THE INVENTION

In accordance with the present invention, human antibodies have been cloned and isolated that demonstrate activity in the promotion, stimulation, regeneration and/or remyelination of neurons in the central nervous system, and/or in the blocking or reduction of demyelination in the central nervous system. Specifically, the present invention relates to methods of stimulating the remyelination of central nervous system (CNS) axons using recombinant autoantibodies, and particularly recombinant human autoantibodies, including antibodies of the IgM subtype and monomers thereof, or mixtures and/or active fragments thereof, characterized by their ability to bind to structures and cells in the central nervous system, particularly including oligodendrocytes.

In a first aspect of the invention, the antibody is a human antibody such as that designated rHIgM22, and the composition includes such antibody in an amount effective to promote remyelination in the central nervous system. The antibody and the corresponding composition are prepared to deliver doses ranging from about 500 ng to about 600 µg, calculated on a per kg of body weight basis. In a particular embodiment, the doses may be on the order of 500 ng, or may be on the order of 600 µg.

In a particular embodiment, the rHIgM22 antibody is administered alone in a pharmaceutically acceptable composition. In another embodiment, the rHIgM22 antibody is administered in combination with methylprednisolone. The methylprednisolone may be administered at doses ranging from about 1 to 2 mg once or twice a week.

In another embodiment, the administration of the rHIgM22 antibody with methylprednisolone may be concurrent or it may be sequential.

A second aspect of the invention provides for pharmaceutical compositions comprising a therapeutically effective amount of the rHIgM22 antibody and a pharmaceutically acceptable carrier. In one embodiment, the composition comprises a therapeutically effective amount of the rHIgM22 antibody alone. In another embodiment, the composition comprises a therapeutically effective amount of the rHIgM22 antibody in combination with a therapeutically effective amount of methylprednisolone. In yet another embodiment, the composition of the rHIgM22 antibody may be formulated as one composition, and the methylprednisolone may be formulated as a separate composition, and each may be delivered to a subject in need of such therapy sequentially or concurrently. In yet another embodiment, the therapeutically effective amount of the rHIgM22 antibody is an amount that promotes remyelination of neurons. In another embodiment, the therapeutically effective amount of the rHIgM22 antibody is an amount that prevents demyelination. In yet another embodiment, the therapeutically effective amount of the rHIgM22 antibody is an amount that decreases demyelination while also promoting remyelination. When used in combination with methylprednisolone, the rHIgM22 antibody may be more effective at preventing demyelination, promoting remyelination or a combination thereof.

A fourth aspect of the invention provides fragments and monomers derived from or related to the recombinant human antibodies of the present invention. Thus, the invention particularly extends to fragments, or monomers derived from or based on sHIgM22 (LYM 22). Such fragments and or monomers possess the same activity as the parent antibody molecule and may demonstrate the capability to remyelinate neurons or to prevent demyelination of neurons.

A fifth aspect of the invention provides an assay for screening other antibodies and related binding partners, including haptens and peptide analogs, that may exhibit a like therapeutic activity. Such activities would include the treatment or prevention of neurological injuries or dysfunctions such as multiple sclerosis, ALS, stroke, Parkinsons disease and Aizheimers disease.

A sixth aspect of the invention provides methods of treating demyelinating diseases in mammals, such as multiple sclerosis in humans, and viral diseases of the central nervous system of humans and domestic animals, such as post-infectious encephalomyelitis, or prophylactically inhibiting the initiation or progression of demyelination in these disease states, using the recombinant monoclonal antibodies, or active fragments thereof, of this invention.

This invention further relates to in vitro methods of producing and stimulating the proliferation of glial cells, such as oligodendrocytes, and the use of these glial cells to treat demyelinating diseases. Accordingly, in one embodiment, the demyelinating neurological condition or disorder for which such antibody therapy would be effective is multiple sclerosis. In another embodiment, the demyelinating neurological condition or disorder for which such antibody therapy would be effective is acute or chronic spinal cord injury. Other neurological conditions or diseases in which demyelination of nerves or nerve fibers is prominent are also contemplated.

The present invention also extends to the cloning, isolation and use of recombinant human autoantibodies that aid in remyelination of neurons or prevent demyelination of neurons, which human autoantibodies are exemplified by rHIgM22. The following terms are used interchangeably throughout this application: RsHIgM22, sHIgM22, rHIgM22 and LYM 22. The heavy and light chain variable region sequences of the recombinant rHIgM22 antibody are set forth in FIGS. 5 and 6 and accordingly, the invention extends to antibodies and corresponding antibody proteins, and small molecules such as haptens, that have or correspond at least in part to the sequences set forth in the noted Figures. These sequences of the antibody may be used in part for cloning the human recombinant form of the antibody, or may be used as probes for research or diagnostic purposes. The invention extends further in that the newly identified recombinant antibodies may be employed for a variety of purposes such as the promotion of remyelination, regeneration of damaged nerve cells, neuronal protection, neuronal outgrowth and the like.

The invention is also broadly directed to peptides which bind to the autoantibodies described herein, whereby these peptides by virtue of their sequence, three-dimensional structure, or conformational changes arising from antibody binding, can be used in and of themselves as peptide vaccines. In a further aspect of the invention, these peptides may have neuromodulatory and/or immunomodulatory properties and may provide a method of inducing a neural cell proliferative response and/or neuroprotective, neuroregenerative and/or remyelinating role in mammals in need of such therapy.

Likewise, the invention includes haptens that may bind to the peptides, the antibodies and/or other relevant substrates and that may possess immunogenicity, so that they may also function as active components in therapeutic formulations, also including vaccines. In a particular embodiment, one or more haptens may be combined with other of the peptides of the present invention, in a vaccine formulation.

In yet a further aspect of the invention these peptides can be formulated as pharmaceutical compositions with stabilizers to prevent proteolytic degradation, thus extending their half-life to be given orally, subcutaneously, intravenously, intranasally, intrathecally or as liposome preparations to mammals in need of such therapy.

In a further aspect, the invention extends to a group of molecules that will be referred to herein as neuromodulatory agents, and that are notable in their therapeutic activity in the CNS. Accordingly, the invention relates to neuromodulatory agents with particular effectiveness in the CNS, which agents comprise a material selected from the group consisting of an antibody of the IgM subtype, a peptide analog, a hapten, active fragments thereof, monomers thereof, agonists thereof, mimics thereof, and combinations thereof. Related antibodies of different subtypes, including those that have undergone a class switch (naturally or as generated by recombinant or synthetic means), are also contemplated, wherein the class switch antibodies have characteristice as neuromodulatory agents useful in the methods of the present invention. The neuromodulatory agents have one or more of the following characteristics: they induce remyelination and/or cellular proliferation of glial cells; and/or evoke $Ca^{++}$ signaling with oligodendrocytes; and/or block cell death, e.g. hydrogen-peroxide induced cell death.

The antibodies of the present invention may be used in conjunction with other antibodies that bind to neural tissue, such as polyclonal antibodies that may also induce remyelination, in particular other polyclonal IgM antibodies, particularly polyclonal IgM immunoglobulin and preparations thereof, more particularly pooled polyclonal IgM immunoglobulin, and pooled polyclonal human IgM immunoglobulin. Preferably, the antibody is a recombinantly produced human antibody or a recombinantly produced chimeric antibody capable of remyelination. In another particular embodiment, the recombinant antibody is rHIgM22 (LYM22), monomers thereof, active fragments thereof, and natural or synthetic antibodies having the characteristics of rHIgM22. The invention provides antibodies comprising a polypeptide having an amino acid sequence corresponding at least in part to a sequence selected from FIGS. 5 and 6, and active fragments thereof.

The present invention also relates to a recombinant DNA molecule or cloned gene, or a degenerate variant thereof, which encodes a class of molecules that will also be referred to herein as neuromodulatory agents, and that include and may be selected from the antibodies of the invention, and particularly antibodies having sequences corresponding at least in part, to the sequences presented in FIGS. 5 and 6; peptides that may correspond at least in part to the antibodies of the present invention, that will also be referred to herein as antibody peptides, and for example, peptides having one or more sequences corresponding at least in part to FIGS. 5 and 6; and small molecules such as haptens; including recombinant DNA molecules or cloned genes having the same or complementary sequences.

The present invention also includes proteins derived from or corresponding to said antibodies, or fragments or derivatives thereof, having the activities noted herein, and that display the amino acid sequences set forth and described above and selected at least in part, from the group consisting of FIGS. 5 and 6.

The present invention likewise extends to haptens that demonstrate the same activities as the proteins or antibody peptides, and that may be administered for therapeutic purposes in like fashion, as by formulation in a vaccine. In one embodiment, a vaccine including both peptides and haptens may be prepared.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present antibody peptides.

In a particular embodiment, the variable region DNA sequence of an antibody of the present invention may be utilized in generating synthetic antibody(ies). In particular, variable region sequence may be combined with its natural or a genetically provided constant region sequence to provide a synthetic antibody. The present invention provides vectors for generating synthetic antibodies derived from and comprising the DNA sequences, particularly variable region sequences, of the antibodies of the present invention.

According to other preferred features of certain preferred embodiments of the present invention, a recombinant expression system is provided to produce biologically active animal or particularly human antibody peptides.

The present invention includes several means for the preparation of clones of the autoantibodies, peptides, corresponding haptens, or other small molecule analogs thereof, including as illustrated herein known recombinant techniques, and the invention is accordingly intended to cover such synthetic preparations within its scope. The isolation of the cDNA and amino acid sequences disclosed herein facilitates the reproduction of the present antibodies or their analogs by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate the neurological activity of target mammalian neural cells by, for example, potentiating the activity of the present autoantibodies or their analogs. In one instance, the test drug could be administered to a cellular sample with the ligand that suppresses or inhibits the activity of the autoantibodies, or an extract containing the suppressed antibodies, to determine its effect upon the binding activity of the autoantibodies to any chemical sample (including DNA), or to the test drug, by comparison with a control.

The present invention includes an assay system which may be prepared in the form of a test kit for the quantitative analysis of the extent of the presence of the neuromodulatory agents, or to identify drugs or other agents that may mimic or block their activity. The system or test kit may comprise a labeled component prepared by one of the radioactive and/or enzymatic techniques discussed herein, coupling a label to the neuromodulatory agents, their agonists and/or antagonists, and one or more additional immunochemical reagents, at least one of which is a free or immobilized ligand, capable either of binding with the labeled component, its binding partner, one of the components to be determined or their binding partner(s).

In a particular and further aspect, the present invention extends to the use and application of the antibodies of the present invention, particularly autoantibodies, including antibodies of the IgM subtype and monomers thereof, or mixtures and/or active fragments thereof, characterized by their ability to bind to structures and cells in the central nervous system, particularly including oligodendrocytes, in imaging and in vivo diagnostic applications. Thus, the antibodies, by virtue of their ability to bind to structures and cells in the central nervous system, particularly including oligodendrocytes, can be utilized via immunofluorescent, radioactive and other diagnostically suitable tags as imaging agents or imaging molecules for the characterization of the nervous system, including the central nervous system and the diagnosis, monitoring and assessment of nervous disease, particularly including multiple sclerosis. The antibodies may further be utilized as imaging agents or imaging molecules in the diagnosis, monitoring and assessment of stroke, spinal cord injury and various dementias including Alzheimer's disease.

In a further embodiment, the present invention relates to certain therapeutic methods which would be based upon the activity of the neuromodulatory agents, their subunits, or active fragments thereof, peptide equivalents thereof, analogs thereof, or upon agents or other drugs determined to possess the same activity. A first therapeutic method is associated with the prevention of the manifestations of conditions causally related to or following from the binding activity of the antibodies or their subunits, and comprises administering an agent capable of stimulating the production and/or activity of the neuromodulatory agents, the corresponding autoantibodies, antibody peptides, active fragments or subunits thereof, either individually or in mixture with each other in an amount effective to prevent or treat the development of those conditions in the host. For example, drugs or other binding partners to the antibodies or their fragments, or the like, may be administered to potentiate neuroregenerative and/or neuroprotective activity, or to stimulate remyelination as in the treatment of multiple sclerosis.

More specifically, the therapeutic method generally referred to herein could include the method for the treatment of various pathologies or other cellular dysfunctions and derangements by the administration of pharmaceutical compositions that may comprise effective inhibitors or enhancers of activation of the neuromodulatory agents, or other equally effective drugs developed for instance by a drug screening assay prepared and used in accordance with an aspect of the present invention discussed above. For example, drugs or other binding partners to the neuromodulatory agents or like proteins, having sequences corresponding at least in part to the sequences as represented by FIGS. 5 and 6, may be administered to inhibit or potentiate neuroregeneration, neuroprotection, or remyelination, as in the treatment of Parkinsons disease or multiple sclerosis. In particular, the proteins of sHIgM22 (LYM22), whose sequence is presented in FIGS. 5 and 6, their antibodies, agonists, antagonists, monomers or active fragments thereof, including mixtures and combinations thereof, could be prepared in pharmaceutical formulations including vaccines, for administration in instances wherein neuroregenerative and/or neuroprotective therapy or remyelination is appropriate, such as to treat Alzheimers disease, ALS, Parkinsons disease, or spinal cord injury. The present invention includes combinations or of the antibodies provided herein, wherein the antibodies, particularly human antibodies, most particularly selected from sHIgM22 can be prepared in pharmaceutical and therapeutic compositions or formulations. Combinations or mixtures of various human antibodies, mouse antibodies, or monomers, fragments, recombinant or synthetic antibodies derived therefrom or based thereon are also provided by and included in the present invention. The human antibodies (extending to monomers, fragments, recombinant or synthetic antibodies derived therefrom) are particularly selected from the group of sHIgM22, sHIgM46, MSI19E10, CB2bG8, AKJR4, CB21E12, CB21E7, MSI19E5, and MSI10E10. The mouse antibodies (extending to monomers, fragments, recombinant or synthetic antibodies and humanized antibodies derived therefrom) are particularly selected from the group of SCH 94.03, SCH79.08, O1, O4, O9, A2B5 and HNK-1. In addition, the invention provides further combinations of the antibody(ies) with therapeutic compounds, drugs or agents useful in any such neuroregenerative and/or neuroprotective therapy or remyelination. For instance, the antibody formulation or composition of the present invention may be combined with therapeutic compounds for the treatment of multiple sclerosis, including but not limited to beta interferon formulations (Betaseron, etc.) and copolymer 1 (Copaxone). In addition, the antibodies of the present invention may be combined with other agents that may act to inhibit inflammation at the site of injury. One such agent may be methylprednisolone.

Accordingly, it is a principal object of the present invention to provide neuromodulatory agents, including the human autoantibodies and corresponding antibody peptides, haptens, analogs and active fragments thereof in purified form that exhibits certain characteristics and activities associated with the promotion of neuroregenerative and/or neuroprotective activity.

It is a further object of the present invention to provide a method for detecting the presence, amount and activity of the autoantibodies in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating any adverse effects of the autoantibodies and/or their fragments, subunits or the like, in mammals.

BRIEF DESCRIPTION OF THE DRAWINGS

FIG. 5 presents the sHIgM22 heavy chain variable region sequences. The sequence is aligned according to the numbering system of human $V_H$ sequences in the publication: Sequences of Proteins of Immunological Interest, Vol I, Fifth Edition (1991), Kabat E. A., Wu, T. T., Perry, H. M. Gottesman, K. S. and Poeller, C., NIH Publication. The sHIgM22 $V_H$ is a member of the $V_H$ subgroup III. Underlined amino acids have been confirmed by protein sequencing. Amino acid sequence corresponds to sHIgM22 nucleotide sequence. SHIgM22 $V_H$ type A and B sequences are represented only with nucleotides that differ from the IGHV3-30/3-30-05*01, IGHJ4*02 and IGHD2-21*02 germline sequences. Two amino acid replacements in the protein sequence of sHIgM22 $V_H$ type B are printed in bold. sHIgM22 antibody heavy chain variable region amino acid sequence is set out in SEQ ID NO: 7, and the nucleic acid sequence is in SEQ ID NO: 8. The sequences of both sHIgM22 $V_H$ type A and B most closely matched the IGHV3-30/3-30-5*01 germline sequence (96% homology). References for germline sequences: IMGT, the international ImMunoGeneTics database [imgt.cnusc]. (Initiator and coordinator: Marie-Paule Lefranc, Montpellier, France)

FIG. 6 presents the sHIgM22 light chain variable region sequences. The sequence is aligned according to the numbering system of human $V_H$ sequences in the publication: Sequences of Proteins of Immunological Interest, Vol I, Fifth Edition (1991), Kabat E. A., Wu, T. T., Perry, H. M. Gottesman, K. S. and Foeller, C., NIH Publication. VX. sHIgM22 is a member of the lambda subgroup I. Underlined amino acids have been confirmed by protein sequencing. Amino acid sequence corresponds to sHIgM22 nucleotide sequence. SHIgM22 Vλ type I and II sequences are represented only with nucleotides that differ from the IGLV1-51*01 and IGLJ3*01 germline sequences. Two amino acid replacements in the protein sequence of sHIgM22 Vλ; type II are printed in bold. sHIgM22 antibody light chain variable region amino acid sequence is set out in SEQ ID NO: 9, and the nucleic acid sequence is in SEQ ID NO: 10. The Vλ sequences from SHIgM22 most closely matched the IGLV-51*01 germline sequence (97% homology). The two genes differ from their common ancestor by a single nucleotide change. References for germline sequences: IMGT, the international ImMunoGeneTics database [imgt.cnusc]. (Initiator and coordinator: Marie-Paule Lefranc, Montpellier, France).

DETAILED DESCRIPTION OF THE INVENTION

Figure 1:
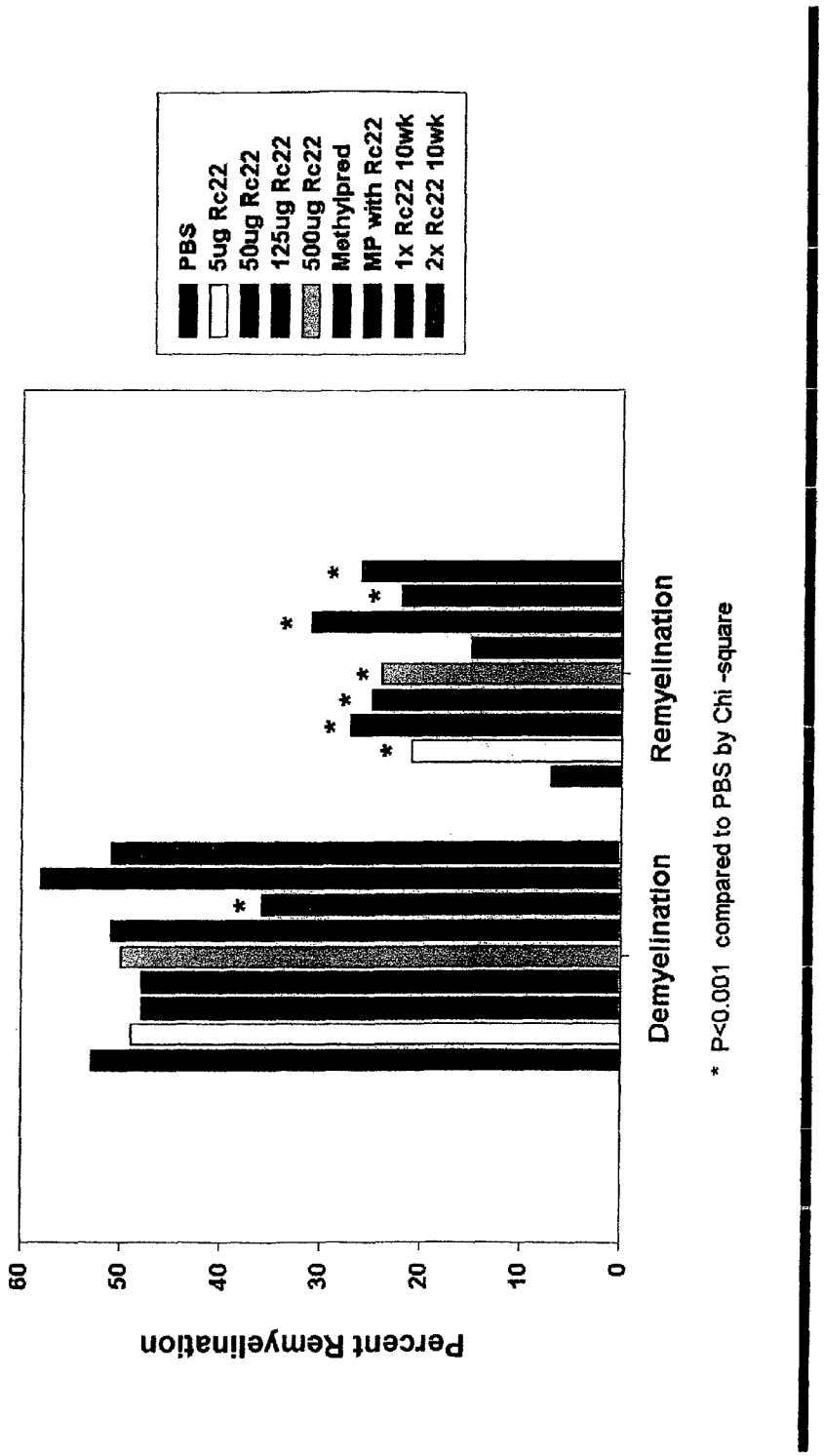
FIG. 1 is a graph of the results of a comparative dose ranging study, with varying concentrations of rHIgM22, placebo, methylprednisolone alone and in combination with rHIgM22.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

DEFINITIONS

Also as used herein, the terms "rHIgM" and "rsHIgM", "sHIgM22" and "LYM22" as pertains to the antibodies of the invention, shall be considered equivalent herein.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease.

The "therapeutically effective amount" can vary depending on the compound, the disease and its severity and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

The term "neuromodulatory agent(s)" as used herein singularly throughout the present application and claims, is intended to refer to a broad class of materials that function to promote neurite outgrowth, regeneration and remyelination with particular benefit and effect in the CNS, and therefore includes the antibodies of the IgM sub-type, and particularly, human antibodies such as those referred to specifically herein as sHIgM22 (LYM 22), ebvHIgM MSI19D10, sHIgM46 (LYM46), CB2bG8, AKJR4, CB2iE12, CB2iE7 and MSI19E5, peptide analogs, haptens, active fragments thereof, monomers thereof, agonists, mimics and the like, including such materials as may have at least partial sequence similarity to the peptide sequences set forth in FIGS. 5 and 6 and in SEQ ID NOS: 7 and 9. Neuromodulatory agent(s) also includes and encompasses combinations or mixtures of more than one of the antibodies provided herein, including monomers or active fragments thereof.

Also, the terms "neuromodulatory agent," "autoantibody," "antibody peptide," "peptide," "hapten" and any variants not specifically listed, may be used herein interchangeably, to the extent that they may all refer to and include proteinaceous material including single or multiple proteins, and extends to those proteins having the amino acid sequence data described herein and presented in FIGS. 5-6 and in SEQ ID NOS: 7 and 9, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "neuromodulatory agent," "autoantibody," "antibody peptide," "peptide," "hapten" are intended where appropriate, to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Gln | glutamic acid |
| W | Trp | tryptophan |
| R | Arg | arginine |
| D | Asp | aspartic acid |
| N | Asn | aspargine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to probes of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. In particular, the heavy chain and light chain variable region sequences of the antibodies of the present invention are substantially homologous to a corresponding germline gene sequence, having at least about 90% homology to a corresponding germline gene sequence.

It should be appreciated that also within the scope of the present invention are DNA sequences encoding an antibody of the invention, or a peptide analog, hapten, or active fragment thereof, which code for a peptide that defines in at least a portion thereof, or has the same amino acid sequence as set forth in FIGS. 5-6 and SEQ ID NOS: 7 and 9, but which are degenerate to the same SEQ ID NOS. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |

-continued

| | |
|---|---|
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in a particular DNA sequence or molecule such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups
Alanine
Valine
Leucine
Isoleucine
Proline
Phenylalanine
Tryptophan
Methionine Amino Acids with Unchargedpolar R Groups
Glycine
Serine
Threonine
Cysteine
Tyrosine
Asparagine
Glutamine Amino Acids with Charged Polar R Groups (Negatively Charged at Ph 6.0)
Aspartic acid
Glutamic acid Basic Amino Acids (Positively Charged at pH 6.0)
Lysine
Arginine
Histidine (at pH 6.0)

Another grouping may be those amino acids with phenyl groups:
Phenylalanine
Tryptophan
Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions. In particular, the heavy chain and light chain variable region sequences of the antibodies of the present invention are substantially homologous to a corresponding germline gene amino acid sequence, having at least about 90%, and preferably at least about 95% homology to a corresponding germline gene amino acid sequence.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the term "antibody" is any immunoglobulin, including antibodies and fragments thereof, that binds a specific epitope. The term is intended to encompass polyclonal, monoclonal, and chimeric antibodies, the last mentioned described in further detail in U.S. Pat. Nos. 4,816,397 and 4,816,567. Such antibodies include both polyclonal and monoclonal antibodies prepared by known generic techniques, as well as bi-specific or chimeric antibodies, and antibodies including other functionalities suiting them for additional diagnostic use conjunctive with their capability of modulating activity, e.g. that stimulates the remyelenation and/or regeneration of CNS axons, or that provides neuroprotection. An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions know in the art as Fab, Fab', F(ab')$_2$ and F(v).

Fab and F(ab')$_2$ portions of antibody molecules, or antibody fragments, may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chains portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

General Description

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)); "Immobilized Cells And Enzymes" PRL Press, (1986)]; B. Perbal, "A Practical Guide To Molecular Cloning" (1984).

Panels of monoclonal antibodies useful in the present invention methods or produced against neuromodulatory agent peptides or autoantibody peptides can be screened for various properties; i.e., isotype, epitope, affinity, etc. Of particular interest are monoclonal antibodies that exhibit the same activity as the neuromodulatory agents, and particularly the present autoantibodies. Such monoclonals can be readily identified in activity assays such as the Theilers virus, EAE and lysolecithin models presented and illustrated herein. High affinity antibodies are also useful when immunoaffinity purification of native or recombinant autoantibodies is possible.

Preferably, the antibody used in the diagnostic methods and therapeutic methods of this invention is an affinity purified polyclonal antibody. More preferably, the antibody is a monoclonal antibody (mAb). In addition, it is contemplated for the antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to an antibody peptide/protein, such as an anti-peptide antibody, preferably an affinity-purified polyclonal antibody, and more preferably a mAb. In addition, it is preferable for the anti-peptide antibody molecules used herein be in the form of Fab, Fab', F(ab')$_2$ or F(v) portions or whole antibody molecules. As previously discussed, patients capable of benefiting from this method include those suffering from a neurological condition such as multiple sclerosis, Alzheimers disease, Parkinsons disease, a viral infection or other like neuropathological derangement, including damage resulting from physical trauma. Methods for isolating the peptides and inducing anti-peptide antibodies and for determining and optimizing the ability of anti-peptide antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab)$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an antibody peptide-binding portion thereof, or the antibody peptide or fragment, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact in the same fashion as the present autoantibodies and their ability to inhibit or promote specified activity in target cells and tissues.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-peptide antibodies are also well-known in the art. See Niman et al., *Proc. Natl. Acad. Sci. USA*, 80:4949-4953 (1983). Typically, the present antibody peptides, or a peptide analog or fragment, is used either alone or conjugated to an immunogenic carrier, as the immunogen in the before described procedure for producing anti-peptide monoclonal antibodies. The hybridomas are screened for the ability to produce an antibody that immunoreacts with the antibody peptide analog and thereby reacts similarly to the antibodies of the present invention.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Polyclonal immunoglobulin preparations have been shown to exert a beneficial clinical effect in various clinical situations that are characterized or accompanied by a dysfunction or dysregulation of the immune system. Immunoglobulin is also used to prevent or treat some illnesses that can occur when an individual does not produce enough of its own immunity to prevent these illnesses. Nearly all immunoglobulin preparations in use today are comprised of highly purified IgG, derived from large pools of human plasma by fractionation. These preparations are commonly administered intravenously (WIG), although intramuscular administration (IGIM) and oral administration is also used.

Commonly used IgG preparations include Gamimune (5% and 10%) (Bayer Corporation), Gammagard (Baxter Healthcare Corporation), Polygam (American Red Cross), Sandoglobin (Sandoz Pharmaceuticals), Venoglobin (Alpha Therapeutic) and Intraglobin (Biotest Pharma GmbH). An intramuscular immunoglobulin (IGIM), BayGam, is available from Bayer Corporation. WIG preparations in clinical use contain predominantly IgG, smaller amounts of IgA, and yet smaller amounts of IgM, IgE and IgD, and generally comprise 95% or greater IgG, 2-5% IgA and trace amounts of IgM.

Pentaglobin (Biotest Pharma GmbH) is an IgM-enriched polyvalent immunoglobulin preparation and each ml of solution comprises: IgM 6 mg; IgA 6 mg; IgG 38 mg and glucose monohydrate for injection 27.5 mg; or 12% IgM, generally 10-15% IgM. Immunoglobulin preparations which have been further enriched for IgM can be readily generated and have been reported as effective in animal models for treatment or alleviation of certain conditions. Riebert et al. report the use of IgM enriched human intravenous immunoglobulin in a rat model of acute inflammation, particularly use of Pentaglobin and a laboratory preparation of IVIgM (35 g/l IgM, 12 g/l IgA, 3 g/l IgG). (Riebert, R. et al (1999) Blood 93(3):942-951). Hurez et al report use of an intravenous IgM preparation of greater than 90% in experimental autoimmune ueveitis (EAU) (Hurez, V. et al (1997) Blood 90(10):4004-4013). IgM antibody immunoglobulin preparations of at least 20% by weight IgM are described in U.S. Pat. Nos. 5,256,771, 5,510,465 and 5,612,033, incorporated herein by reference in their entity. Intravenously administrable polyclonal immunoglobulin preparations containing at least 50% by weight of IgM in terms of the total content of immunoglobulin are described by Moller et al in U.S. Pat. No. 5,190,752, incorporated herein by reference in its entirety.

Immunoglobulin preparations are generated by methods and processes generally well known to those of skill in the art. Immunoglobulins are prepared from blood of healthy volunteers, where the number of blood donors is at least about 5 or 10; preferably at least about 100; more preferably at least about 1,000; still more preferably at least about 10,000. In one common method, human plasma derived from pools of thousands of donors is fractionated by cold ethanol fractionation (the Cohn process or Cohn-Oncley process) (Cohn, et al (1946) J. Am. Chem. Soc. 68:459-475; Oncley, et al (1949) J. Am. Chem. Soc. 71:541-550) followed by enzymatic treatment at low pH, fractionation and chromatography. Cold ethanol fractionation may also be followed by ultrafiltration and ion exchange chromatography. Further steps are incorporated to render immunoglobulin preparations safe from viral transmission, including but not limited to enzymatic modification, chemical modification, treatment with beta-propiolactone, treatment at low pH, treatment at high heat and treatment with solvent/detergent. Treatment with an organic solvent/detergent (S/D) mixture eliminates viral transmission by enveloped viruses (HIV, hepatitis B, hepatitis C) (Gao, F. et al (1993) Vox Sang 64(4):204-9; U.S. Pat. Nos. 4,481,189 and 4,540,573, incorporated herein by reference). Particular processes and methods for preparation of IgM enriched immunoglobulin solutions are described in U.S. Pat. Nos. 4,318,902 and 6,136,132, which are incorporated herein by reference in their entirety.

Polyclonal IgM-enriched immunoglobulin preparations contemplated herein and suitable for use in the methods of the present invention can be made by any of the well-known methods used for preparing immunoglobulin preparations. Suitable immunoglobulin preparations can also be obtained commercially. The immunoglobulin preparation can be a human immunoglobulin preparation. Suitable immunoglobulin preparations include at least about 10% IgM, at least about 15% IgM, at least about 20% IgM, at least about 25% IgM, at least about 30% IgM, at least about 40% IgM, at least about 50% IgM, at least about 60% IgM, at least about 70% IgM, at least about 80% IgM, at least about 90% IgM and at least about 95% IgM. Polyclonal IgM immunoglobulin preparations suitable for use in the present invention include greater 10% IgM, greater than 20% IgM, and greater than 50% IgM. Polyclonal IgM immunoglobulin preparations suitable for use in the present invention include an amount of IgM which is greater than the amount if IgG and greater than the amount of IgA.

Preparations of fragments of IgM enriched immunoglobulins, particularly human immunoglobulins can also be used in accordance with the present invention. Fragments of immunoglobulins refer to portions of intact immunoglobulins such as Fc, Fab, Fab', F(ab)'$_2$ and single chain immunoglobulins or monomers.

The IgM-enriched immunoglobulin preparation in preferably provided in a pharmaceutically acceptable carrier, vehicle or diluent and is administered intravenously, intramuscularly or orally. IgM immunoglobulin is administered in doses and amounts similar to the administration recognized and utilized by the skilled artisan for the administration of clinically adopted immunoglobulins, including WIG or IGIM or Pentaglobin, or as instructed or advised clinically or by the manufacturer. In accordance with a central aspect of the invention, the recombinant IgM preparations are administered in doses as determined in mice, of from about 500 ng to about 600 µg. By adjusting these amounts for adaptation to humans, taking into account both the size of the subject and differences in surface to volume, the approximate range would be from about 1.25 to about 2.5 µg/kg body weight. Administration can be conducted in a single dose or in multiple separated or divided doses daily or over the course of days or months. Suitable dosages include 1.25 µg/kg body weight, 1.3 µg/kg body weight, 1.4 µg/kg body weight, 1.5 µg/kg body weight, 1.6 µg/kg body weight, 1.7 µg/kg body weight, 1.8 µg/kg body weight, 1.9 µg/kg body weight, 2.0 µg/kg body weight, 2.1 µg/kg body weight, 2.2 µg/kg body weight, 2.3 µg/kg body weight, 2.4 µg/kg body weight, and 2.5 µg/kg body weight. The polyclonal IgM immunoglobulin preparations may be administered alone or in combination with other treatments, including but not limited to other compounds or agents for treatment or alleviation of the condition. In the instance of treatment or alleviation of a demyelinating disease, multiple sclerosis in particular, the IgM immunoglobulin may be administered with anti-inflammatories, steroids, Betaseron, Copaxone, etc.

Accordingly, in one aspect of the diagnostic application of the present invention, a method is disclosed for detecting the presence or activity of a neuromodulatory agent, the neuromodulatory agent comprising a material selected from the group consisting of an antibody, a peptide analog, a hapten, monomers thereof, active fragments thereof, agonists thereof, mimics thereof, and combinations thereof, said neuromodulatory agent having one or more of the following characteristics: inducing remyelination; binding to neural tissue; promoting $Ca^{++}$ signaling with oligodendrocytes; and, optionally, promoting cellular proliferation of glial cells; wherein said neuromodulatory agent is measured by:

A) contacting a biological sample from a mammal in which the presence or activity of said neuromodulatory agent is suspected with a binding partner of said neuromodulatory agent under conditions that allow binding of said neuromodulatory agent to said binding partner to occur; and B) detecting whether binding has occurred between said neuromodulatory agent from said sample and the binding partner;

wherein the detection of binding indicates that presence or activity of the neuromodulatory agent in the sample.

In a variant aspect, the invention extends to a method for detecting the presence and activity of a polypeptide ligand associated with a given invasive stimulus in mammals comprising detecting the presence or activity of the neuromodulatory agent as set forth above, where detection of the presence or activity of the neuromodulatory agent indicates the presence and activity of a polypeptide ligand associated with a given invasive stimulus in mammals. In a particular aspect, the invasive stimulus is an infection, and may be selected from viral infection, protozoan infection, bacterial infection, tumorous mammalian cells, and toxins.

In a further aspect, the invention extends to a method for detecting the binding sites for a neuromodulatory agent, said neuromodulatory agent comprising a material selected from the group consisting of an antibody, including antibodies of the IgM subtype and monomers thereof, a peptide analog, a hapten, active fragments thereof, agonists thereof, mimics thereof, and combinations thereof, said neuromodulatory agent having one or more of the following characteristics: inducing remyelination; binding to neural tissue; promoting $Ca^{++}$ signaling with oligodendrocytes; and, optionally, promoting cellular proliferation of glial cells; said method comprising:

A. placing a labeled neuromodulatory agent sample in contact with a biological sample from a mammal in which binding sites for said neuromodulatory agent are suspected;

B. examining said biological sample in binding studies for the presence of said labeled neuromodulatory agent;

wherein the presence of said labeled neuromodulatory agent indicates a binding site for a neuromodulatory agent.

Yet further, the invention includes a method of testing the ability of a drug or other entity to modulate the activity of a neuromodulatory agent, said agent comprising a material selected from the group consisting of an antibody, including antibodies of the IgM subtype, a peptide analog, a hapten, monomers thereof, active fragments thereof, agonists thereof, mimics thereof, and combinations thereof, which method comprises:

A. culturing a colony of test cells which has a receptor for the neuromodulatory agent in a growth medium containing the neuromodulatory agent;

B. adding the drug under test; and

C. measuring the reactivity of said neuromodulatory agent with the receptor on said colony of test cells;

wherein said neuromodulatory agent has one or more of the following characteristics:

a) inducing remyelination;
b) binding to neural tissue, particularly oligodendrocytes;
c) promoting $Ca^{++}$ signaling with oligodendrocytes; and
d) promoting cellular proliferation of glial cells.

Correspondingly, the invention covers an assay method for screening drugs and other agents for ability to modulate the production or mimic the activities of a neuromodulatory agent, said neuromodulatory agent comprising a material selected from the group consisting of an antibody, a peptide analog, a hapten, monomers thereof, active fragments thereof, agonists thereof, mimics thereof, and combinations thereof, said method comprising:

A. culturing an observable cellular test colony inoculated with a drug or agent;

B. harvesting a supernatant from said cellular test colony; and

C. examining said supernatant for the presence of said neuromodulatory agent wherein an increase or a decrease in a level of said neuromodulatory agent indicates the ability of a drug to modulate the activity of said neuromodulatory agent, said neuromodulatory agent having one or more of the following characteristics:

i) inducing remyelination;
ii) binding to neural tissue, particularly oligodendrocytes;
iii) promoting $Ca^{++}$ signaling with oligodendrocytes; and
iv) promoting cellular proliferation of glial cells.

Lastly, a test kit is contemplated for the demonstration of a neuromodulatory agent in a eukaryotic cellular sample, said neuromodulatory agent comprising a material selected from the group consisting of an antibody, including antibodies of the IgM subtype and monomers thereof, a peptide analog, a hapten, active fragments thereof, agonists thereof, mimics thereof, and combinations thereof, which kit comprises:

A. a predetermined amount of a detectably labeled specific binding partner of a neuromodulatory agent, said neuromodulatory agent having one or more of the following characteristics: inducing remyelination; binding to neural tissue; promoting $Ca^{++}$ signaling with oligodendrocytes; and promoting cellular proliferation of glial cells;

B. other reagents; and

C. directions for use of said kit.

A variant test kit is disclosed for demonstrating the presence of a neuromodulatory agent in a eukaryotic cellular sample, said agent comprising a material selected from the group consisting of an antibody, a peptide analog, a hapten, monomers thereof, active fragments thereof, agonists thereof, mimics thereof, and combinations thereof. The kit comprises:

A. a predetermined amount of a neuromodulatory agent, said neuromodulatory agent having one or more of the following characteristics: inducing remyelination; binding to neural tissue; promoting $Ca^{++}$ signaling with oligodendrocytes; and promoting cellular proliferation of glial cells;

B. a predetermined amount of a specific binding partner of said neuromodulatory agent;

C. other reagents; and

D. directions for use of said kit;

wherein either said neuromodulatory agent or said specific binding partner are detectably labeled. Both of the above kits may utilize a labeled immunochemically reactive component selected from the group consisting of polyclonal antibodies to the neuromodulatory agent, monoclonal antibodies to the neuromodulatory agent, fragments thereof, and mixtures thereof.

The present invention extends to the use and application of the antibodies of the present invention, particularly autoantibodies, including antibodies of the IgM subtype and monomers thereof, or mixtures and/or active fragments thereof, characterized by their ability to bind to structures and cells in the central nervous system, particularly including oligodendrocytes, in imaging and in vivo diagnostic applications. Thus, the antibodies, by virtue of their ability to bind to structures and cells in the central nervous system, particularly including oligodendrocytes, can be utilized via immunofluorescent, radioactive and other diagnostically suitable tags as imaging agents or imaging molecules for the characterization of the nervous system, including the central nervous system and the diagnosis, monitoring and assessment of nervous disease, particularly including multiple sclerosis. The antibodies may further be utilized as imaging agents or imaging molecules in the diagnosis, monitoring and assessment of stroke, spinal cord injury and various dementias including Alzheimer's disease. The appropriate and suitable immunofluorescent, radioactive, or other tagging molecules or agents for coupling or attachment to the antibodies for use in in vivo imaging will be well known to and within the skill of the skilled artisan.

The present invention also relates to methods of treating demyelinating diseases in mammals, such as multiple sclerosis in humans, and viral diseases of the central nervous system of humans and domestic animals, such as post-infectious encephalomyelitis, using the recombinant human antibody described herein as rHIgM22 as well as SCH 94.03, SCH 79.08, O1, O4, A2B5 and HNK-1 monoclonal antibodies, and the human autoantibodies ebvHIgM MSI19D10, sHIgM46, analogs thereof including haptens, active fragments thereof, or a natural or synthetic autoantibody having the characteristics thereof. Methods of prophylactic treatment using these mAb, active fragments thereof, or other natural or synthetic autoantibodies having the same characteristics, to inhibit the initiation or progression demyelinating diseases are also encompassed by this invention.

Oligodendrocytes (OLs), the myelin-forming cells of the central nervous system (CNS), originate as neuroectodermal cells of the subventricular zones, and then migrate and mature to produce myelin. The sequential development of OLs is identified by well-characterized differentiation stage-specific markers. Proliferative and migratory bipolar precursors, designated oligodendrocyte/type-3 astrocyte (O-2A) progenitors, are identified by monoclonal antibodies (mAbs) anti-$GD_3$ and A2B5 [Eisenbarth et al., Proc. Natl. Acad. Sci. USA, 76 (1979), 4913-4917]. The next developmental stage, characterized by multipolar, postmigratory, and proliferative cells, is recognized by mAb O4 [Gard et al., Neuron, 5 (1990), 615-625; Sommer et al., Dev. Biol., 83 (1981), 311-327]. Further development is defined by the cell surface expression of galactocerebroside, recognized by mAb O1 [Schachner, J. Neurochem., 39 (1982), 1-8; Sommer et al., supra], and by the expression of 2',3'-cyclic nucleotide 3'-phosphohydrolase. The most mature cells express terminal differentiation markers such as myelin basic protein and proteolipid protein.

The mAbs (A2B5, O1, and O4) used to characterize the stages of OL development were made by immunizing BALB/c mice with chicken embryo retina cells or homogenate of bovine corpus callosum [Eisenbarth et al., supra; Sommer et al., supra]. A2B5 recognizes not only O-2A progenitors but also neurons and reacts with cell surface ganglioside GQ1c [Kasai et al., Brain Res., 277 (1983), 155-158] and other gangliosides [Fredman et al., Arch. Biochem. Biophys., 233 (1984), 661-666]. O4 reacts with sulfatide, seminolipid and cholesterol [Bansal et al., J. Neurosci. Res., 24 (1989), 548-557], whereas O1 reacts with galactocerebroside, monogalactosyl-diglyceride and psychosine [Bansal et al., supra]. These mAbs belong to the IgM immunoglobulin (Ig) subclass and recognize cytoplasmic structures as well as the surface antigens of OLs [Eisenbarth et al., supra; Sommer et al., supra]. Mouse mAb HNK-1 (anti-Leu-7), made by immunizing BALB/c mice with the membrane suspension of HSB-2 T lymphoblastoid cells, was first reported as a marker for natural killer cells [Abo et al., J. Immunol., 127 (1981), 1024-1029]. Later, HNK-1 was shown to share antigenic determinants with the nervous system [Schuller-Petrovic et al., Nature, 306 (1983), 179-181]. The carbohydrate epitope on myelin-associated glycoprotein, found in both central and peripheral myelin sheaths, was shown to be a principal antigen of nervous tissue the reacted with FINK-1 [McGarry et al., Nature, 306 (1983), 376-378]. However, other glycoproteins in nervous tissue react with this mAb, some of which are important in embryogenesis, differentiation, and myelination [Keilhauer et al., Nature, 316 (1985), 728-730; Kruse et al., Nature, 311 (1984), 153-155; Kruse et al., Nature, 316 (1985), 146-148; McGarry et al., J. Neuroimmunol., 10 (1985), 101-114]. Of interest, HNK-1 also reacts with cytoplasmic structures and belongs to the IgM Ig subclass.

A monoclonal antibody, disclosed and claimed by certain of the inventors of the present application in application U.S. Ser. No. 08/236,520, incorporated herein by reference in its entirety, which antibody is designated SCH94.03, was found to promote CNS remyelination in mice infected chronically with Theiler's murine encephalomyelitis virus (TMEV) [Miller et al., J. Neurosci., 14 (1994), 6230-6238]. SCH94.03 belongs to the IgM($\varkappa$) Ig subclass and recognizes an unknown surface antigen on OLs, but cytoplasmic antigens in all cells (Asakura et al., Molecular Brain Research, in press). The polyreactivity of SCH94.03 by ELISA, and the unmutated Ig variable region germline sequences indicated that SCH94.03 is a natural autoantibody [Miller et al., J. Neurosci., 14 (1994), 6230-6238]. A close study of SCH94.03, and comparison thereof with well-known OL-reactive mAbs A2B5, O1, O4, and FINK-1 raised the possibility that these are natural autoantibodies. A subsequent analysis of the Ig variable region cDNA sequences and the polyreactivity of these mAbs by ELISA confirmed that this is a generic group of natural autoantibodies having similar utilities.

The antigen reactivity of the monoclonal antibody, IgM monoclonal antibody referred to herein as SCH 94.03 (also referred to herein as SCH94.32) and SCH 79.08 (both prepared from a mammal immunized with spinal cord homogenate from a normal mammal (i.e., uninfected with any demyelinating disease)), have been characterized and described in the aforesaid application U.S. Ser. No. 08/236,520, filed Apr. 29, 1994, whose teachings are incorporated herein by reference, using several biochemical and molecular assays, including immunohistochemistry, immunocytochemistry, Western blotting, solid-phase enzyme-linked immunosorbant assays (ELISA), and Ig variable region sequencing. The hybridomas producing monoclonal antibody SCH 94.03 and SCH 79.08 have been deposited on Apr. 28, 1994 and Feb. 27, 1996, respectively, under the terms of the Budapest Treaty, with the American Type Culture Collection (ATCC) and have been given ATCC Accession Nos. CRL 11627 and HB12057, respectively. All restrictions upon the availability of the deposit material will be irrevocably removed upon granting of a patent.

Natural or physiologic autoantibodies are present normally in serum, are characterized by being reactive or capable of binding to self structures, antigens or cells. They are often polyreactive, are frequently of the IgM subtype, and are encoded by unmutated germline genes or are substantially homologous to germline genes with few or several sequence differences. By sequencing immunoglobulin (Ig) cDNAs of the oligodendrocyte-reactive O1, O4, A2B5, and HNK-1 IgM $\varkappa$ monoclonal antibodies and comparing these with published germline sequences, it was determined that these were natural autoantibodies. O1 $V_H$ was identical with unrearranged $V_H$ segment transcript A1 and A4, O4 $V_H$ had three and HNK-1 $V_H$ had six nucleotide differences from $V_H 101$ in the $V_H$ coding region. The D segment of O1 was derived from germline SP2 gene family, $J_H 4$, whereas O1 $J_H$ was encoded by germline $J_H 1$ with one silent nucleotide change. O1 and O4 light chains were identical with myeloma MOPC21 except for one silent nucleotide change. HNK-1 V$\varkappa$ was identical with germline V$\varkappa$41 except for two silent nucleotide changes. O1 J$\varkappa$, O4J$\varkappa$ and HNK J$\varkappa$ were encoded by unmutated germline J$\varkappa$2. In contrast, A2B5 $V_H$ showed seven nucleotide differences from germline V1, whereas no germline sequence encoding A2B5 V$\varkappa$ was identified. O1 and O4, but not A2B5 were polyreactive against multiple antigens by direct ELISA. Therefore, O1, O4 and HNK-1 Igs are encoded by germline genes, and have the genotype and phenotype of natural autoantibodies.

Treatment of Demyelinating Diseases

The results of the experiments described herein have practical applications to multiple sclerosis (MS), EAE, and other related central nervous system demyelinating disorders. Rare examples of spontaneous CNS-type remyelination ("shadow plaques") are found in MS and occasional peripheral nervous system (PNS)-type remyelination is found in demyelinated spinal cord plaques near the root entry zone. Oligodendrocytes are infrequent at the center of the chronic plaques in MS but they appear to proliferate at the periphery of plaques, where they are associated with abortive remyelination. The process of remyelination may correlate with the spontaneous remission and improvements observed clinically in MS. These clinical observations indicate that new myelin formation is possible in MS. The remyelination that has been stimulated in mice with TMEV-induced demyelination by using a mAb holds promise for therapeutic applications in multiple sclerosis.

Of importance clinically is the question of whether morphologic regeneration of thin myelin sheaths contributes to functional recovery. Computer simulations indicate that new myelin formation even by inappropriately thin sheaths improves impulse conduction. Since the axon membrane of normally myelinated fibers is highly differentiated, it is necessary for sodium channels to be present at high density at the node of Ranvier to propagate salutatory conduction. Experimental evidence suggests that newly formed nodes do develop the required high sodium channel density as demonstrated by saxitoxin binding. Data to date suggest that remyelination even by inappropriately thin myelin improves conduction in a previously demyelinated axon. Therefore, any strategy to promote this morphologic phenomenon has the potential of producing functional recovery.

The data presented herein demonstrates, for the first time, that administration of a recombinant human monoclonal antibody to a mammal is capable of stimulating remyelination of central nervous system axons in vivo. Specifically, treatment of chronically infected TMEV-infected mice with as little as 500 ng of rHIgM22 resulted in a significant increase in the total area of CNS myelination compared to mice treated with a control mAb.

The use of human antibodies avoids the potential for human immune response against the therapeutic antibody. Therapeutic antibodies derived from non-human animals have been shown to generate an immune response, which can be significant and detrimental to the individual. Accordingly, polyclonal human IgM and polyclonal human IgG have been tested in two models of in vivo spinal cord demyelination; a chronic viral infection model, and an acute toxicity model. In both models polyclonal human IgM treated animals had a significantly higher density of newly myelinated axons than animals treated with polyclonal human IgG. A panel of human monoclonal IgM antibodies have also been identified, based on their reactivity with surface antigens specific to the central nervous system. These human antibodies promote significantly more central nervous system remyelination than polyclonal human IgG when given to mammals with demyelinating disease. The human monoclonal antibodies are antigenically polyreactive and recognize determinants on the surface of oligodendrocytes and specific populations of neurons. The light and heavy chain variable regions of several human antibodies that promote remyelination have been sequenced. In particular, these antibodies can induce calcium fluxes in glial cells (oligodendrocytes and astrocytes) in culture, suggestive of direct binding and signaling through glial cells. These human antibodies bind to human white matter and may be effective in promoting remyelination in humans. The benefits of a recombinant monoclonal antibody for use as a therapeutic agent are 1) the antibody can be grown free of possible host infection and, 2) the antibody can be genetically altered in vitro to change its effectiveness.

Thus, as a result of the experiments described herein, the method of the present invention can be used to treat mammals, including humans and domestic animals, afflicted with demyelinating disorders, and to stimulate remyelination and regeneration of the CNS axons, as well as to offer neuroprotection. As described herein, an effective amount of the monoclonal antibody or a peptide fragment, hapten, or equivalent, can be administered by conventional routes of administration, and particularly by, intravenous (iv) or intraperitoneal (ip) injection. As described herein, therapeutic compositions and vaccines are contemplated and may be prepared and administered. An effective amount of the antibody can vary depending on the size of the mammal being treated, the severity of the disease, the route of administration, and the course of treatment. For example, each dose of antibody administered can range from approximately 1.25 to about 2.5 µg/kg, as an exemplary, non limiting range in accordance with the present invention. The dose of antibody will also depend on the route of administration. The course of treatment includes the frequency of administration of the antibody (e.g., daily, weekly, or bi-weekly) and the duration of the treatment (e.g., four weeks to four months). Thus, for example, a larger amount of mAb can be given daily for four to five weeks, as opposed to a smaller amount of mAb given for four months.

The effectiveness of the amount of the monoclonal antibody being administered can be assessed using any number of clinical criteria, for example, as described in the Examples herein, including overall appearance of the mammal, the activity of the mammal and the extent of paralysis of the mammal. The effectiveness of the amount of monoclonal antibody necessary to induce remyelination in humans can also be assessed in a double blinded controlled trial. Patients with fixed neurological deficits from demyelinating disease can be treated with monoclonal antibody or controls. Improvement in isometric muscle strength as detected by quantitative biomechanics muscle testing could be used as the primary therapeutic end-point.

In addition to in vivo methods of promoting remyelination, ex vivo methods of stimulating remyelination in CNS axons are also encompassed by the present invention. For example, the monoclonal antibody may be used in vitro to stimulate the proliferation and/or differentiation of glial cells, such as oligodendrocytes. These exogenous glial cells can then be introduced into the CNS of mammals using known techniques. Remyelination of CNS axons would be increased by increasing the number of endogenous glial cells present (glial cells, such as oligodendrocytes play a critical role in the production of myelin).

In vitro methods of producing glial cells, or stimulating the proliferation of glial cells from mixed culture (e.g., rat optic nerve cell, or rat brain cell cultures) are also encompassed by this invention. For example, cells obtained from rat optic nerve, or rat brain, containing glial cells, are cultured as a mixed culture under conditions sufficient to promote growth of the cells. An effective amount of mAb capable of promoting remyelination of CNS axons, such as rHIgM22 or sHIgM46, or SCH94.03 or a combination thereof, is then added to the mixed culture of cells and maintained under conditions sufficient for growth and proliferation of cells. The mAb stimulates the proliferation of glial cells cultured in the presence of the mAb is increased, relative to the proliferation of glial cells grown in the absence of the mAb.

As stated above, the antibodies for use in the methods of the present invention can be, and are preferably, administered as medicaments, i.e., pharmaceutical compositions. An effective amount of the polyclonal IgM antibody can thus be combined with, or diluted with, an appropriate pharmaceutically acceptable carrier, diluent or vehicle, such as a physiological buffer or saline solution. An effective amount of the monoclonal antibody can thus be combined with, or diluted with, an appropriate pharmaceutically acceptable carrier, diluent or vehicle, such as a physiological buffer, or saline solution. An effective amount of a combination of one or more monoclonal antibody may be similarly combined with or diluted with an appropriate pharmaceutically acceptable carrier, diluent or vehicle. In the instance where a vaccine is to be prepared, the monoclonal antibody or equivalent active of the invention may be prepared with a pharmaceutically effective and suitable carrier or adjuvant, and the protocol for administration may proceed in accordance with standard procedures for immunization known to the skilled practitioner.

The pharmaceutical compositions used in the methods of this invention for administration to animals and humans comprise the polyclonal IgM antibodies or monoclonal antibodies in combination with a pharmaceutical carrier or excipient. In a preferred embodiment, the pharmaceutical composition may contain more than one, preferably two, monoclonal autoantibodies of the present invention. Thus, pharmaceutical compositions comprising, for example, an effective amount in combination of sHIgM22 and sHIgM46 are contemplated herein. Such compositions are advantageous in that the presence of more than one monoclonal autoantibody will potentiate the activity of others in the same therapeutic composition or method.

The medicament can be in the form of tablets (including lozenges and granules), dragees, capsules, pills, ampoules or suppositories comprising the compound of the invention.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian.

The monoclonal antibodies can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (g) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,1-butylene glycol, dimethylformamide, oils (for example, ground nut oil, glycerol, tetrahydrofurfuryl alcohol, polyethylene glycols and fatty acid esters of sorbitol or mixtures thereof.

For parental administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil), and sweetening agents, (e.g., saccharin and aspartame).

The pharmaceutical compositions will generally contain from 0.5 to 90% of the active ingredient by weight of the total composition.

In addition to the monoclonal antibodies, the pharmaceutical compositions and medicaments can also contain other pharmaceutically active compounds, e.g. steroids, anti-inflammatory agents or the like.

Any diluent in the medicaments of the present invention may be any of those mentioned above in relation to the pharmaceutical compositions. Such medicaments may include solvents of molecular weight less than 200 as the sole diluent.

It is envisaged that the polyclonal IgM antibodies and monoclonal antibodies will be administered perorally, parenterally (for example, intramuscularly, intraperitoneally, subcutaneously, transdermally or intravenously), rectally or locally, preferably orally or parenterally, especially perlingually, or intravenously.

The administered dosage rate will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

According to the invention, the component or components of a therapeutic composition of the invention may be introduced parenterally, intrathecally, transmucosally, e.g., orally, nasally, pulmonarally, or rectally, or transdermally. Preferably, administration is parenteral, e.g., via intravenous injection, and also including, but is not limited to, intra-arterial, intramuscular, intradermal, subcutaneous, intraperitoneal, intraventricular, and intracranial administration. Oral or pulmonary delivery may be preferred to activate mucosal immunity; since the bacteria responsible for the conditions under treatment generally colonize the nasopharyngeal and pulmonary mucosa, mucosal administration may be particularly effective as a treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, Science 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site of inappropriate immune activation or a tumor. Other controlled release systems are discussed in the review by Langer (Science 249: 1527-1533 (1990)).

A subject in whom administration of an active component as set forth above is an effective therapeutic regimen for a condition or pathology associated with the central nervous system, including in certain instances, bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with Other Compounds

For treatment of a demyelinating condition, for instance multiple sclerosis, one may administer the present active component in conjunction with one or more pharmaceutical compositions used for treating multiple sclerosis, including but not limited to (1) anti-inflammatory agents, such as steroids; (2) Betaseron; (3) Copaxone; or 94) polyclonal IgM, or 4) methylprednisolone. Administration may be simultaneous (for example, administration of a mixture of the present active component and an antibiotic), or may be in seriatim.

Accordingly, in specific embodiment, the therapeutic compositions may further include an effective amount of the active component, and one or more of the following active ingredients: an antibiotic, a steroid, etc.

Also contemplated herein is pulmonary delivery of the present neuromodulatory agent or agents, which may be associated with an anti-inflammatory. Reports of preparation of proteins for pulmonary delivery are found in the art [Adjei et al. *Pharmaceutical Research,* 7:565-569 (1990); Adjei et al., *International Journal of Pharmaceutics,* 63:135-144 (1990) (leuprolide acetate); Braquet et al., *Journal of Cardiovascular Pharmacology,* 13(suppl. 5):143-146 (1989) (endothelin-1); Hubbard et al., *Annals of Internal Medicine,* Vol. III, pp. 206-212 (1989) (α1-antitrypsin); Smith et al., *J. Clin. Invest.* 84:1145-1146 (1989) (α-1-proteinase); Oswein et al., "Aerosolization of Proteins", *Proceedings of Symposium on Respiratory Drug Delivery II,* Keystone, Colo., March, (1990) (recombinant human growth hormone); Debs et al., *J. Immunol.* 140:3482-3488 (1988) (interferon-γ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of adhesin inhibitory agent (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified adhesin inhibitory agent may also be prepared in different formulations depending on the type of chemical modification or the type of device employed.

Formulations suitable for use with a nebulizer, either jet or ultrasonic, will typically comprise neuromodulatory agent (or derivative) dissolved in water at a concentration of about 0.1 to 25 mg of biologically active agent per ml of solution. The formulation may also include a buffer and a simple sugar (e.g., for neuromodulatory agent stabilization and regulation of osmotic pressure). The nebulizer formulation may also contain a surfactant, to reduce or prevent surface induced aggregation of the neuromodulatory agent caused by atomization of the solution in forming the aerosol.

Formulations for use with a metered-dose inhaler device will generally comprise a finely divided powder containing the neuromodulatory agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain neuromodulatory agent and a dispersing agent in a physiologically acceptable diluent. The dry powder aerosol formulations of the present invention consist of a finely divided solid form of neuromodulatory agent and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L., *Crit. Rev. in Ther. Drug Carrier Systems* 8:333 (1991)].

The neuromodulatory agents of the invention may also be prepared for administration in the form of vaccines, which may comprise as the active, the herein recited autoantibodies, peptide analogs, or haptens, or possibly combinations thereof. Thus, the preparation of vaccines may proceed in accordance with known procedures, and monovalent as well as polyvalent vaccines are contemplated. Also, DNA sub unit vaccines, based upon the DNA molecules of the invention, may be prepared. All vaccines may be administered in accordance with standard practices of the physician or clinician, and such parameters are considered to be within the scope of the present invention.

Vectors containing e.g. a DNA-based vaccine in accordance with the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

The vaccine can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal target for retroviral vector-based nucleic acid vaccines, since retroviruses require replicating cells.

Passive immunity can be conferred to an animal subject suspected of suffering an autoimmune-mediated demyelinating disease, e.g. multiple sclerosis, by administering antiserum, polyclonal antibodies, or a neutralizing monoclonal antibody to the patient. Preferably, the antibodies administered for passive immune therapy are autologous antibodies. For example, if the subject is a human, preferably the antibodies are of human origin or have been "humanized," in order to minimize the possibility of an immune response against the antibodies. The active or passive vaccines of the invention, or the administration of an adhesin, can be used to protect an animal subject from infection of a Gram positive bacteria, preferably streptococcus, and more preferably, pneumococcus.

Further, the present invention contemplates treatment by gene therapy, where the appropriate neuromodulatory agent is correspondingly introduced to target cells for treatment, to cause or increase expression of the corresponding agent. Thus, in one embodiment, the DNA or a gene encoding the neuromodulatory agent, autoantibody, antibody peptide, etc., or a protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and therapy procedures are DNA-based vectors and retroviral vectors. Methods for constructing and using viral vectors are known in the art [see, e.g., Miller and Rosman, *BioTechniques* 7:980-990 (1992)].

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., *Molec. Cell. Neurosci.* 2:320-330 (1991)], defective herpes virus vector lacking a glycoprotein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [*J. Clin. Invest.* 90:626-630 (1992); see also La Salle et al., *Science* 259:988-990 (1993)]; and a defective adeno-associated virus vector [Samulski et al., *J. Virol.* 61:3096-3101 (1987); Samulski et al., *J. Virol.* 63:3822-3828 (1989); Lebkowski et al., *Mol. Cell. Biol.* 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the DNA or gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980, 289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845. Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner, et. al.,

*Proc. Natl. Acad. Sci. U.S.A.* 84:7413-7417 (1987); see Mackey, et al., *Proc. Natl. Acad. Sci. U.S.A.* 85:8027-8031 (1988); Ulmer et al., *Science* 259:1745-1748 (1993)]. The use of cationic lipids may promote encapsulation of negatively charged nucleic acids, and also promote fusion with negatively charged cell membranes [Feigner and Ringold, *Science* 337:387-388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990; Williams et al., *Proc. Natl. Acad. Sci. USA* 88:2726-2730 (1991)]. Receptor-mediated DNA delivery approaches can also be used [Curiel et at., *Hum. Gene Ther.* 3:147-154 (1992); Wu and Wu, *J. Biol. Chem.* 262: 4429-4432 (1987)].

In a preferred embodiment of the present invention, a gene therapy vector as described above employs a transcription control sequence that comprises the DNA consensus sequence recognized by e.g. an autoantibody of the invention, i.e., an antibody binding site, operably associated with a therapeutic heterologous gene inserted in the vector. That is, a specific expression vector of the invention can be used in gene therapy.

The present invention will be better understood from a consideration of the following non-limiting examples, which describe the preparation of materials, compounds and compositions and the development and practice of methods illustrative of the present invention. It will be apparent to those skilled in the art that many modifications, both of materials and methods, may be practiced without departing from the purpose and intent of this disclosure. The following examples are presented in order to more fully illustrate the preferred embodiments of the invention and serve also in fulfillment of applicants' duty to present the best mode known for the practice of the invention, and should in no way be construed as limiting the broad scope thereof.

EXAMPLES

Example 1

Dose Ranging Study using Recombinant sHIgM22 (Study #1) Mice 4-6 weeks old female SJL/J mice from the Jackson Laboratories were injected intracerebrally with $2\times10^5$ plaque-forming units of Daniel's strain TMEV in 10 µl. Infected animals received a single 500 µl intraperitoneal (IP) injection of rHIgM22 at various concentrations, or PBS 6 months after TMEV infection. One group received an additional 500 µg dose of rHIgM22 after 5 weeks. Two groups of mice received 2 mg of methylprednisolone once each week. Ten mice were used for each group. Animals were killed for quantitative analysis of remyelination in the spinal cords after 5 or 10 week of treatment.

Figure 2:
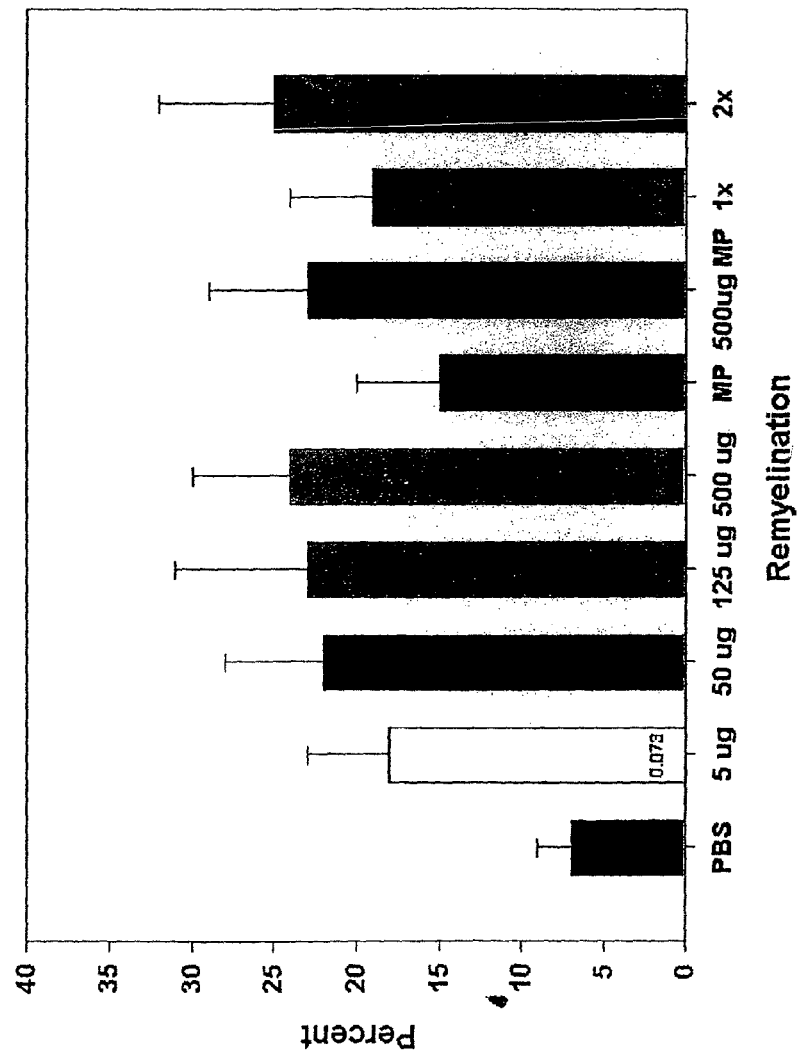
FIG. 2 is a graph of the mean scores of the test subject groups in the dose ranging study.

To determine the minimum effective dose, a dose-ranging study of RsHIgM22 was performed in mice chronically infected with TMEV. After 5 wk of treatment, spinal cords were removed and graded for demyelination and remyelination. The results are directly presented in FIG. 1, and a comparison of mean values of the scores categorized as to subjects receiving the same dosing, is presented in FIG. 2.

From a review of the results, all doses of RsHIgM22 down to 0.25 mg/kg resulted in significantly greater area of remyelination than saline controls ($p<0.001$ by ANOVA). This demonstrates the ability of the antibodies of the invention to offer therapeutically relevant effects at reasonable dosing.

In addition, animals treated with RsHIgM22 and 2 mg of methylprednisolone per week presented with less demyelination ($p<0.001$) by ANOVA as well as increased remyelination. This is significant because steroids are a primary method of treatment for many patients with acute exacerbations, who would be potential recipients of remyelinating human mAbs. Moreover, these results suggest that the aspect of the invention pertaining to the preparation and administration of a composition comprising a steroid such as methylprednisolone, and the antibodies of the invention, or alternatively the formulation and administration of a composition comprising the steroid and the antibody for separate but conjoint or sequential administration, can yield the advantageous results demonstrated herein.

These results demonstrate that RsHIgM22 can act at concentrations in the range of those required for classic growth factors.

Example 2

Testing the Effectiveness of rHIgM22 Alone at Lower Doses or in Combination with Methylprednisolone (Study #2)

Materials and Methods
Mice
4-6 weeks old female SJL/J mice from the Jackson Laboratories were injected intracerebrally with $2\times10^5$ plaque-forming units of Daniel's strain TMEV in 10 µl. Infected animals received a single 5000 intraperitoneal (IP) injection of rHIgM22 at various concentrations, or PBS 6 months after TMEV infection. One group received an additional 500 µg dose of rHIgM22 after 5 weeks. Two groups of mice received 1 mg of methylprednisolone twice each week. Ten mice were used for each group. Animals were killed for quantitative analysis of remyelination in the spinal cords after 5 or 10 week of treatment.

Antibody Isolation and Sequencing

IgM antibody was isolated from the serum (designated sHIgM22) of a patient with Waldenström's macroglobulinemia and was sequenced as described (Ciric, B. et al (2000), Blood 97: 321-323).

Cloning and Testing of rHIgM22
Vector Construction
1) Light Chain Fragment
The light chain variable region (VL) was amplified from a TA-cloned VL fragment derived from an antibody mRNA isolated from peripheral blood leukocytes of patient who was the source of sHIgM22. A 5'-Nhe I site, 5'-UTR and artificial leader sequence from a human IgM sequence in the human genome database (Tsujimoto, Y. et al. (1984), Nucleic Acids Res. 12: 8407-8414) were added to this sequence. The constant region of λ-chain (Cλ) was amplified from human blood cDNA with additional 3'-Avr II site that is found in human Cλ. All polymerase chain reactions (PCRs) were performed by the standard methods by using the following primers designed for one identified form of the predominant IgM species (designated light chain: II) found in sHIgM22 (Ciric, B. et al (2000), Blood 97: 321-323).:

```
ctagctagccgaatttcgggacaatcttcatcatgacctgctcccctctc ctcctcacccttctcattcactgcacagggtcctgggcccagtctgtgtt gacgcagccg (SEQ ID NO: 6)

3'-primer of VL:
                                           (SEQ ID NO: 1)
gggcagccttgggctgacctaggacggtcagc 5'-primer of Cλ:
                                           (SEQ ID NO: 2)
ctagctagcgtcctaggtcagcccaaggctgccccc 3'-primer of Cλ:
                                           (SEQ ID NO: 3)
atagtttagcggccgcacctatgaacattctgtagg
```

2) Heavy Chain Fragment

Human IgM genomic sequence was isolated and cloned by adding two unique sites on both ends of VH (5': Rsr II,3': PacI. VH was amplified from TA-coned sHIgM22 VH region with additional artificial 5'-UTR, and leader sequence from the human genome database (11) by using the primers of:

```
5'-primer of VH:
                                           (SEQ ID NO: 4)
gactcggaccgcccagccactggaagtcgccggtgtttccattcggtgat catcactgaacacagaggactcaccatggagtttggctgagctgggtttt cctcgttgctcttttaagaggtgtccagtgtcaggtgcagctggtggagt ctgg 3'-primer of VH:
                                           (SEQ ID NO: 5)
ccttaattaagacctggagaggccattcttacctgaggagacggtgacca gggttc
```

VH of the human IgM was replaced by this amplified VH fragment of sHIgM11.

3) Dehydroxy Folic Acid Reductase Gene (dhfr) Fragment

The dhfr fragment was amplified from the vector pFR2000 (Simonsen, C. et al. (1983), PNAS USA 80: 2495-2499) by standard PCR reaction and was ligated into pCICλ. The HIgM22II light chain combined with dhfr was produced by EagI digestion of pCICλ, and this fragment was ligated into the Eag I site in sHIgM22 VH vector (pDM 22BII). The gene order of this pDM 22B11 vector was 1) heavy chain (genomic), 2) light chain (cDNA), and 3) dhfr. The heavy chain and light chain genes were oriented in the same direction but that of dhfr was opposite.

Electroporation, Methotrexate (MTX) Amplification, ELISA, and IgM Purification pDM 22BII was transfected into 2×10 7 of F3B6 cells by electroporation; 10 g of pMD22BII linearized by Bgl II was mixed with 2×10 7 of F3B6 cells, resuspended in 800l of ice-cold serum-free RPMI on ice for 10 min, pulsed once at 960 F/200V with Bio-Rad Gene Pulser (Bio-Rad, Hercules, Calif.), returned to ice for 30 min, transferred to a 25-cm 2 flask, fed with 5 ml of RPMI with 10% fetal calf serum, and incubated in 5% CO2 at 37 ûC. After incubation for 48 h, the medium was replaced by fresh medium containing 0.2 µM of MTX, and incubation continued until survival colonies appeared. These colonies were transferred to a 24-well plate and were cultured in 1 M MTX. ELISA was performed for these clones after confluent growth as described below, and positive clones were chosen for further manipulation. NUNC Maxisorp™ plates were coated with 20 µg/ml goat anti-human IgA+IgM+IgG (H+ L) (ICN Pharmaceuticals, Inc., Colta Mesa, Calif.). Following a blocking step with 1% bovine serum albumin (BSA; Sigma-Aldrich Co., St. Louis, Mo.), supernatants from sHIgM22BII expressing F3B6 cells were plated in duplicate at 1:500, 1:1000, and 1:2000 dilutions. Purified Human IgM (Organon Teknika Corp. West Chester, Pa.) was used as the standard control. After incubation and washes with phosphate buffered saline (PBS)/1% Tween 20, monoclonal anti-human IgM conjugated to alkaline phosphatase (Sigma-Aldrich Co.) was applied at a 1:5000 dilution in 1% BSA. Positive reactions were detected by using p-Nitrophenyl Phosphate (Sigma-Aldrich Co.), and absorbance was read on a Bio-Rad microplate reader at 405 nm. MTX concentration was increased geometrically starting from 0.2 µM and ended at 200 ìM over a course of 2 months. The highest antibody-producing clone was determined by ELISA, and the culture media of this clone was Collected. IgM antibody of recombinant sHIgM22BII was isolated from this media by the methods of PEG6000 (Fluka, Buchs, Switzerland) precipitation and dialysis against H2O, followed by size fractionation over a Superose 6 column.

Evaluation of Spinal Cord for Demyelination/Remyelination

Regions of demyelination and remyelination of the spinal cord were visualized using 4% para-phenylenediamine stained plastic embedded cross sections. To obtain a representative sampling of the entire spinal cord, 1 µm thick cross sections were cut from every third serial 1 mm block. This generated 10 to 12 cross sections that represent samples from the cervical, thoracic, lumbar, and sacral spinal cord. For grading each spinal cord section was divided visually into four quadrants, then each quadrant was scored for the presence or absence of a demyelinated or remyelinated lesion. All slides were coded and read blind. Data was not assembled into treatment groups until all slides were graded. Lesions were judged to be remyelinated when the entire lesion was essentially repaired. Partially remyelinated lesions were scored as negative. Levels of remyelination were calculated as follows: (the number of quadrants with remyelination/the number of total demyelinated quadrants)×100. The categorical data were evaluated using a Chi-square statistical analysis.

Immunohistochemistry

Adult SJL mouse cerebellar slice sections were prepared as described previously (Warrington, A. et al. (1992), J. Neurosci Res. 33:338-353). Briefly, a fresh cerebellum was embedded in 3% low melting temperature agarose, mounted on a #2 Whatman filter, and cut into 300 µm saggital slices. Slices were then transferred to 48-well tissue culture plates. Following a 2- to 3-h incubation with 5% BSA in N-(2-hydroxyethyl)piperazine-N-ethanesulfonic acid (HEPES) buffered Earle™s balanced salt solution (E/H, pH 7.4), the slices were labeled with primary antibodies at 10 µg/ml in 1% BSA in E/H, for at least 3 h with gentle rocking at 4° C. After being washed with E/H, the slices were stained with appropriate secondary antibodies, washed, and then fixed briefly with 4% paraformaldehyde in PBS. Slides were mounted in MOWIOL (Aldrich Chemical, Milwaukee, Wis.) containing 2.5% 1,4-diazobicyclo-[2.2.2]-octane (DABCO, Sigma, St. Louis, Mo.) and viewed with an epifluorescence microscope. Mixed primary glial cells and purified oligodendrocytes were prepared from Sprague-Dawley rat neonates as previously described (Asakura, K. et al. (1997), J. Neurochem 68: 2281-2290). Cells were plated on poly-D-lysine-coated or poly-L-ornithine glass coverslips. Live surface staining was performed at 4 ûC for 15 min on unfixed cells after blocking with E/H containing 3% normal goat serum. Bound primary antibodies (Abs) were detected with fluorescence-conjugated secondary Abs. Slides were mounted and viewed as described above.

Purification of rHIgM22 rHIgM22-transfected F3B6 cells were grown in roller bottles in RPMI/10% heat-inactivated FBS/penicillin/streptomycin/glutamine supplemented with 10 μM methotrexate (MTX). Conditioned medium was concentrated by tangential flow filtration (TFF) to 0.2 mg/ml of protein. Concentrated conditioned medium was dialyzed overnight against dH$_2$O to precipitate IgM antibodies. Pellet was resuspended in 50 mM Tris (Trizma base), pH 8.0, 150 mM NaCl, 0.5% w/v betaine. The resuspended pellet was loaded onto a Sephacryl S-300 (26/60) column and eluted with 20 mM Tris, pH 8.0, 200 mM NaCl, 0.5% betaine. The elution profile consisted of ~2 major peaks: HMW (~80%) and LMW (~20%). Pentameric IgM was found in the BMW peak. Pooled GF fractions were concentrated to ~0.5 mg/ml (A$_{280}$) and dialyzed against 20 mM sodium phosphate, 200 mM NaCl, pH8.0 (final formulation buffer).

Results

Figure 3:
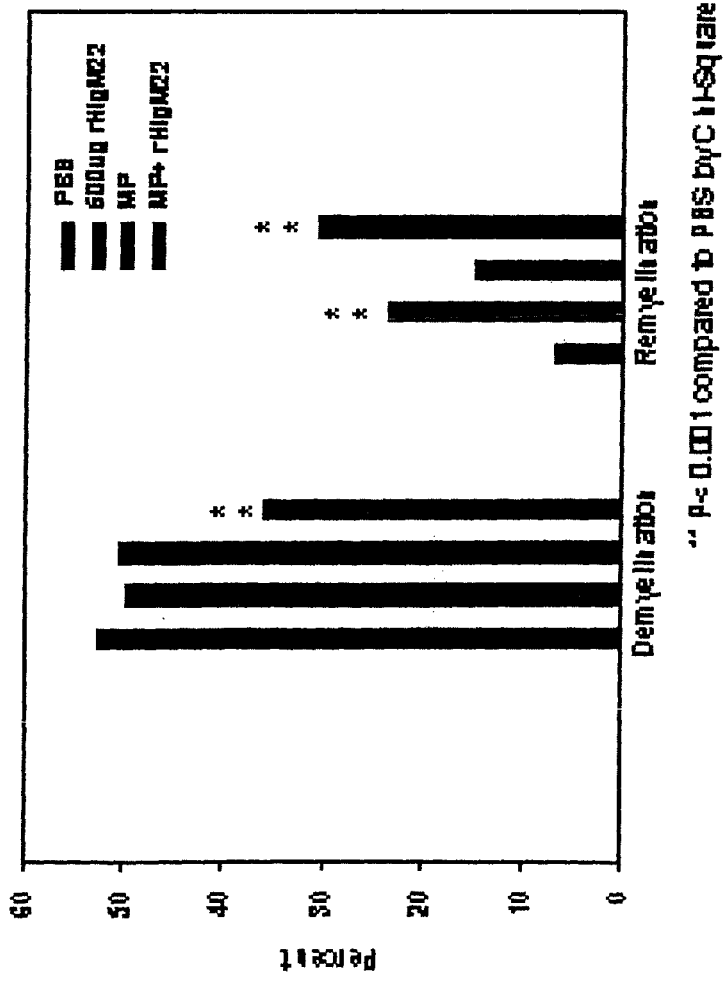
FIG. 3 is a graph demonstrating that rHIgM22 combined with methylprednisolone promotes remyelination and reduces lesion load.
Figure 4:
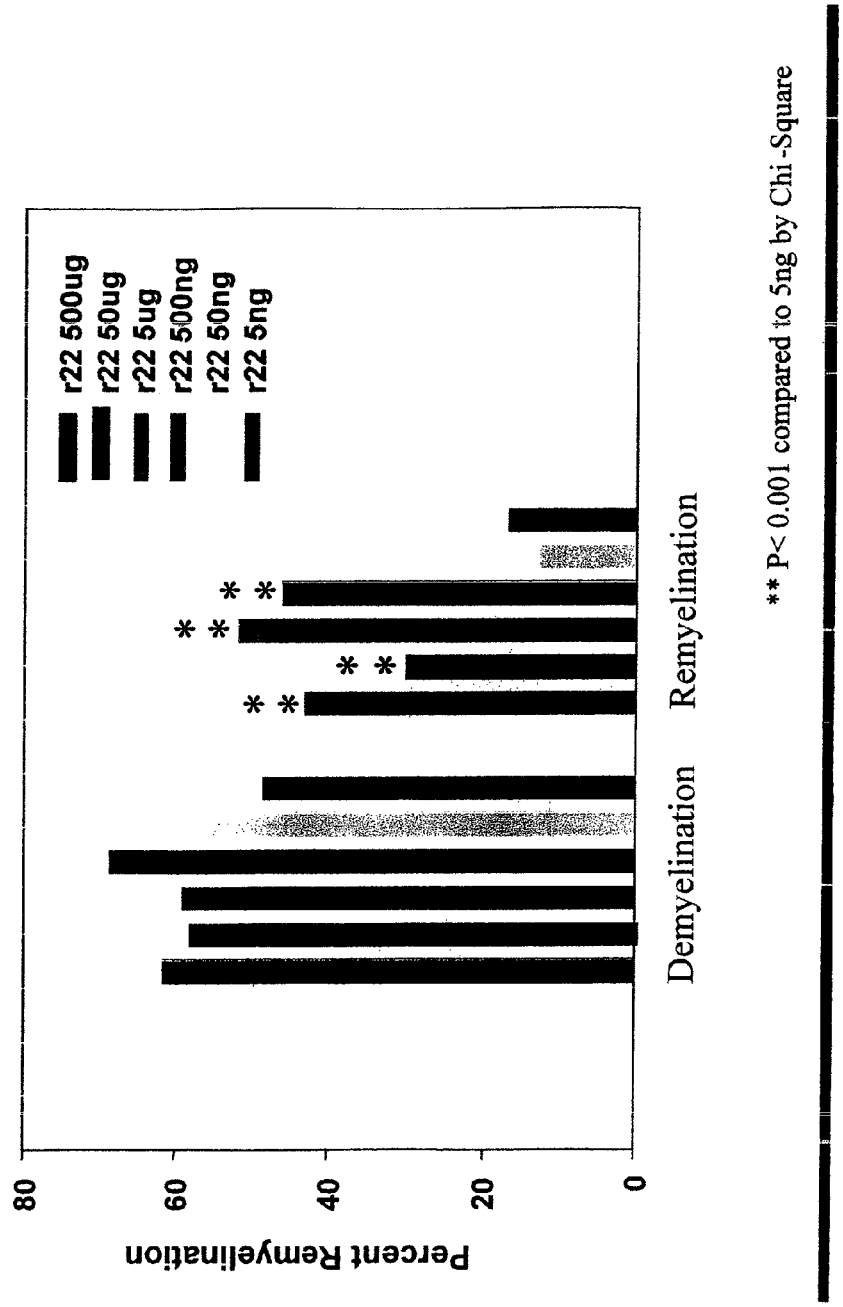
FIG. 4 is a graph of the results of a comparative dose ranging study with varying concentrations of rHIgM22.

In this experiment, further studies were conducted to determine whether effective dosing could be achieved with greater reductions in concentration of the antibody as either the sole active ingredient, or in combination with a steroid such as methylprednisolone. The results establish that even greater reductions and consequent advantages in dosing are possible (FIGS. 3 and 4). RHIgM22 was effective at preventing demyelination at a dose of 600 μg when combined with methylprednisolone (FIG. 3). Furthermore, rHIgM22 was significantly effective at remyelination at doses as low as 500 ng (FIG. 4) when used alone, and also demonstrated even greater remyelination capabilities when administered at a dose of 600 μg when combined with methylprednisolone.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A composition for use in in vivo imaging and diagnostic applications comprising an antibody, said composition comprising:
   an antibody capable of stimulating remyelination and comprising the heavy chain variable region CDR1, CDR2 and CDR3 sequences as set out in FIG. 5 and SEQ ID NO:7 and the light chain variable region CDR1, CDR2 and CDR3 sequences as set out in FIG. 6 and SEQ ID NO:9; the antibody selected from the group consisting of: a human monoclonal antibody mAb sHIgM22 (LYM 22), active fragments thereof, or recombinant antibodies derived therefrom; and
   an immunofluorescent, radioactive or other diagnostically suitable tag as the imaging agent;
   wherein said composition is prepared for delivery in humans in a dose range of 1.25 μg antibody/kg body weight to 2.5 μg antibody/kg body weight.

2. The composition of claim 1 wherein said composition is prepared for delivery in humans at a dose of said antibody/kg body weight selected from the group of: 1.25 μg antibody/kg body weight, 1.3 μg/kg, 1.4 μg/kg, 1.5 μg/kg, 1.6 μg/kg, 1.7 μg/kg, 1.8 μg/kg, 1.9 μg/kg, 2.0 μg/kg, 2.1 μg/kg, 2.2 μg/kg, 2.3 μg/kg, 2.4 μg/kg, and 2.5 μg/kg body weight.

3. A composition for use in in vivo imaging and diagnostic applications comprising an antibody, said composition comprising:
   an antibody capable of stimulating remyelination and comprising the heavy chain variable region CDR1, CDR2 and CDR3 sequences as set out in FIG. 5 and SEQ ID NO:7 and the light chain variable region CDR1, CDR2 and CDR3 sequences as set out in FIG. 6 and SEQ ID NO:9; the antibody selected from the group consisting of: a human monoclonal antibody mAb sHIgM22 (LYM 22), active fragments thereof, or recombinant antibodies derived therefrom; and
   an immunofluorescent, radioactive or other diagnostically suitable tag as the imaging agent;
   wherein said composition is prepared for delivery in humans in a single dose of the antibody of 500 ng.

4. The composition of any of claims 1-3 wherein the antibody is labeled for detection in vivo with one or more radioisotope, magnetic resonance shift reagent or radio-opaque reagent.

5. The composition of any of claims 1-3 wherein said antibody comprises a heavy chain variable region amino acid sequence as set out in FIG. 5 and SEQ ID NO: 7 and a light chain variable region amino acid sequence as set out in FIG. 6 and SEQ ID NO: 9.

6. A method for characterizing the central nervous system and for diagnosis, monitoring and assessment of central nervous system disease in a mammal comprising in vivo imaging and diagnostics of the central nervous system comprising administering to said mammal a composition comprising:
   an antibody capable of stimulating remyelination and comprising the heavy chain variable region CDR1, CDR2 and CDR3 sequences as set out in FIG. 5 and SEQ ID NO:7 and the light chain variable region CDR1, CDR2 and CDR3 sequences as set out in FIG. 6 and SEQ ID NO:9; the antibody selected from the group consisting of: a human monoclonal antibody mAb sHIgM22 (LYM 22), active fragments thereof, or recombinant antibodies derived therefrom; and
   an immunofluorescent, radioactive or other diagnostically suitable tag as the imaging agent;
   wherein said composition is prepared for delivery in said mammal in a dose range of 1.25 μg antibody/kg body weight to 2.5 μg antibody/kg body weight.

7. The method of claim 6 wherein said composition is prepared for delivery in said mammal at a dose of said antibody/kg body weight selected from the group of: 1.25 μg antibody/kg body weight, 1.3 μg/kg, 1.4 μg/kg, 1.5 μg/kg, 1.6 μg/kg, 1.7 μg/kg, 1.8 μg/kg, 1.9 μg/kg, 2.0 μg/kg, 2.1 μg/kg, 2.2 μg/kg, 2.3 μg/kg, 2.4 μg/kg, and 2.5 μg/kg body weight.

8. The method of claim 6, wherein the administering step comprises administration in a single dose.

9. The method of claim 6, wherein the administering step comprises administration in multiple separated or divided doses.

10. A method for characterizing the central nervous system and the diagnosis, monitoring and assessment of central nervous system disease in a mammal comprising in vivo imaging and diagnostics of the central nervous system comprising administering said mammal a composition comprising:
    an antibody capable of stimulating remyelination and comprising the heavy chain variable region CDR1, CDR2 and CDR3 sequences as set out in FIG. 5 and SEQ ID NO:7 and the light chain variable region CDR1, CDR2 and CDR3 sequences as set out in FIG. 6 and SEQ ID NO:9; the antibody selected from the group consisting of: a human monoclonal antibody mAb sHIgM22 (LYM 22), active fragments thereof, or recombinant antibodies derived therefrom; and
    an immunofluorescent, radioactive or other diagnostically suitable tag as the imaging agent;
    wherein said composition is prepared for delivery in humans in a single dose of the antibody of 500 ng.

11. The method of claim 6 or 10 wherein the antibody is labeled for detection in vivo with one or more radioisotope, magnetic resonance shift reagent or radio-opaque reagent.

12. The method of claim 6 or 10 wherein said mammal is a human having multiple sclerosis, or a human or domestic animal with a demyelinating disease, or a disease or other injury or dysfunction of the central nervous system.

13. The method of claim 6 or 10 wherein said antibody comprises a heavy chain variable region amino acid sequence as set out in FIG. 5 and SEQ ID NO: 7 and a light chain variable region amino acid sequence as set out in FIG. 6 and SEQ ID NO: 9.

* * * * *

SEQUENCE LISTING

<160> NUMBER OF SEQ ID NOS: 10

<210> SEQ ID NO 1
<211> LENGTH: 32
<212> TYPE: DNA
<213> ORGANISM: Artificial Sequence
<220> FEATURE:
<223> OTHER INFORMATION: 3' primer

<400> SEQUENCE: 1
gggcagcctt gggctgacct aggacggtca gc                                    32

<210> SEQ ID NO 2
<211> LENGTH: 36
<212> TYPE: DNA
<213> ORGANISM: Artificial Sequence
<220> FEATURE:
<223> OTHER INFORMATION: 5' primer

<400> SEQUENCE: 2
ctagctagcg tcctaggtca gcccaagget gccccc                                36

<210> SEQ ID NO 3
<211> LENGTH: 36
<212> TYPE: DNA
<213> ORGANISM: 3Artificial Sequence
<220> FEATURE:
<223> OTHER INFORMATION: 3' primer

<400> SEQUENCE: 3
atagtttagc ggccgcacct atgaacattc tgtagg                                36

<210> SEQ ID NO 4
<211> LENGTH: 154
<212> TYPE: DNA
<213> ORGANISM: Artificial Sequence
<220> FEATURE:
<223> OTHER INFORMATION: 5' primer -continued

<400> SEQUENCE: 4
gactcggacc gcccagccac tggaagtcgc cggtgtttcc attcggtgat catcactgaa        60
cacagaggac tcaccatgga gtttggctga gctgggtttt cctcgttgct cttttaagag       120
gtgtccagtg tcaggtgcag ctggtggagt ctgg                                   154

<210> SEQ ID NO 5
<211> LENGTH: 56
<212> TYPE: DNA
<213> ORGANISM: Artificial Sequence
<220> FEATURE:
<223> OTHER INFORMATION: 3' primer

<400> SEQUENCE: 5
ccttaattaa gacctggaga ggccattctt acctgaggag acggtgacca gggttc            56

<210> SEQ ID NO 6
<211> LENGTH: 110
<212> TYPE: DNA
<213> ORGANISM: Artificial Sequence
<220> FEATURE:
<223> OTHER INFORMATION: 5' primer

<400> SEQUENCE: 6
ctagctagcc gaatttcggg acaatcttca tcatgacctg ctcccctctc ctcctcaccc        60
ttctcattca ctgcacaggg tcctgggccc agtctgtgtt gacgcagccg                  110

<210> SEQ ID NO 7
<211> LENGTH: 119
<212> TYPE: PRT
<213> ORGANISM: Homo sapiens
<220> FEATURE:
<221> NAME/KEY: VARIANT
<222> LOCATION: 50
<223> OTHER INFORMATION: Xaa can be Val or Ile
<221> NAME/KEY: VARIANT
<222> LOCATION: 89
<223> OTHER INFORMATION: Xaa can be Asp or Glu

<400> SEQUENCE: 7

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Ser
            20                  25                  30

Gly Met His Trp Val Arg Gln Ala Pro Gly Lys Gly Leu Glu Trp Val
        35                  40                  45

Ala Xaa Ile Ser Tyr Asp Gly Ser Arg Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Thr Ala Xaa Asp Thr Ala Val Tyr Tyr Cys
                85                  90                  95

Ala Lys Gly Val Thr Gly Ser Pro Thr Leu Asp Tyr Trp Gly Gln Gly
            100                 105                 110

Thr Leu Val Thr Val Ser Ser
        115

<210> SEQ ID NO 8
<211> LENGTH: 357
<212> TYPE: DNA
<213> ORGANISM: Homo sapiens

```
<220> FEATURE:
<221> NAME/KEY: variation
<222> LOCATION: 27
<223> OTHER INFORMATION: n is a or g
<221> NAME/KEY: variation
<222> LOCATION: 117
<223> OTHER INFORMATION: n is g or a

<400> SEQUENCE: 8
caggtgcagc tggtggagtc tgggggnggc gtggtccagc ctgggaggtc cctgagactc      60
tcctgtgcag cctctggatt caccttcagt agctctggca tgcactgggt ccgccangct     120
ccaggcaagg gctggagtg gtggcagtt atatcatatg atggaagtaa taaatactat      180
gcagactccg tgaagggccg attcaccatc tccagagaca attccaagaa cacgctgtat     240
ctgcaaatga acagcctgag agctgaggac acggctgtgt attactgtgc gaaagaggtg     300
actgctattc cctactttga ctactgggc cagggaaccc tggtcaccgt ctcctca        357

<210> SEQ ID NO 9
<211> LENGTH: 114
<212> TYPE: PRT
<213> ORGANISM: Homo sapiens
<220> FEATURE:
<221> NAME/KEY: VARIANT
<222> LOCATION: 46
<223> OTHER INFORMATION: Xaa is Arg or Lys
<221> NAME/KEY: VARIANT
<222> LOCATION: 90
<223> OTHER INFORMATION: Xaa is Gly or Glu

<400> SEQUENCE: 9

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
             20                  25                  30

Phe Val Ser Trp Tyr Gln Gln Leu Pro Gly Thr Ala Pro Xaa Leu Leu
         35                  40                  45

Ile Tyr Asp Ile Thr Lys Arg Pro Ser Gly Ile Pro Asp Arg Phe Ser
     50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Xaa Thr Trp Asp Ser Ser Leu
                 85                  90                  95

Ser Ala Val Val Phe Gly Gly Gly Thr Lys Leu Thr Val Leu Gly Gln
            100                 105                 110

Pro Lys

<210> SEQ ID NO 10
<211> LENGTH: 342
<212> TYPE: DNA
<213> ORGANISM: Homo sapiens
<220> FEATURE:
<221> NAME/KEY: variation
<222> LOCATION: 137
<223> OTHER INFORMATION: n is g or a
<221> NAME/KEY: variation
<222> LOCATION: 269
<223> OTHER INFORMATION: n is g or a

<400> SEQUENCE: 10
cagtctgtgt tgacggagcc gccttcagtg tctgctgccc caggacagaa ggtcaccatc      60
tcctgctctg gaagcagctc caacattggc aataattttg tatcctggta ccagcaactc     120
```

| | | | | | |
|---|---|---|---|---|---|
| ccaggaacag | cccccanact | cctcatttat | gacattacta | agcgaccctc | agggattcct | 180 |
| gaccgattct | ctggctccaa | gtctggcacg | tcagccaccc | tgggcatcac | cggactccag | 240 |
| actggggacg | aggccgatta | ttactgcgna | acatgggata | gcagcctgag | tgctgtggta | 300 |
| ttcggcgggg | ggaccaagct | gaccgtccta | ggtcagccca | ag | | 342 |